US 8,178,124 B2

(12) United States Patent
Niitsu et al.

(10) Patent No.: US 8,178,124 B2
(45) Date of Patent: May 15, 2012

(54) DRUG CARRIER AND DRUG CARRIER KIT FOR INHIBITING FIBROSIS

(75) Inventors: Yoshiro Niitsu, Sapporo (JP); Junji Kato, Sapporo (JP); Yasushi Sato, Sapporo (JP)

(73) Assignee: Nitto Denko Corporation, Ibaraki, Osaka (JP)

(*) Notice: Subject to any disclaimer, the term of this patent is extended or adjusted under 35 U.S.C. 154(b) by 0 days.

(21) Appl. No.: 13/249,072

(22) Filed: Sep. 29, 2011

(65) Prior Publication Data

US 2012/0076852 A1    Mar. 29, 2012

Related U.S. Application Data

(62) Division of application No. 11/793,736, filed as application No. PCT/JP2005/023619 on Dec. 22, 2005.

(30) Foreign Application Priority Data

Dec. 22, 2004 (JP) ................................. 2004-382791

(51) Int. Cl.
*A61K 9/127* (2006.01)
*A61K 9/14* (2006.01)
*A61K 31/07* (2006.01)
*C12N 15/11* (2006.01)

(52) U.S. Cl. ....... 424/450; 424/489; 514/44 A; 514/725; 514/893

(58) Field of Classification Search .......................... None
See application file for complete search history.

(56) References Cited

U.S. PATENT DOCUMENTS

| 4,966,773 A | 10/1990 | Gressel et al. |
| 5,643,584 A | 7/1997 | Farng et al. |
| 5,827,886 A | 10/1998 | Hersh |

(Continued)

FOREIGN PATENT DOCUMENTS

JP    5-503076    5/1993

(Continued)

OTHER PUBLICATIONS

AK Singh, "Liposome encapsulated vitamin A compounds exhibit greater stability and diminished toxicity." Biophysical Chemistry, Vo. 73, 1998, pp. 155-162.

(Continued)

*Primary Examiner* — Frederick Krass
*Assistant Examiner* — Isaac Shomer
(74) *Attorney, Agent, or Firm* — Knobbe Martens Olson & Bear LLP

(57) ABSTRACT

An astrocyte-specific drug carrier containing a retinoid derivative and/or a vitamin A analog as a constituent; a drug delivery method with the use of the same; a drug containing the same; and a therapeutic method with the use of the drug. By binding a drug carrier to a retinoid derivative such as vitamin A or a vitamin A analog or encapsulating the same in the drug carrier, a drug for therapeutic use can be delivered specifically to astrocytes. As a result, an astrocyte-related disease can be efficiently and effectively inhibited or prevented while minimizing side effects. As the drug inhibiting the activity or growth of astrocytes, for example, a siRNA against HSP47 which is a collagen-specific molecule chaperone may be encapsulated in the drug carrier. Thus, the secretion of type I to type IV collagens can be inhibited at the same time and, in its turn, fibrosis can be effectively inhibited.

14 Claims, 24 Drawing Sheets

U.S. PATENT DOCUMENTS

| | | | |
|---|---|---|---|
| 5,851,538 | A | 12/1998 | Froix et al. |
| 6,183,774 | B1 | 2/2001 | Aust et al. |
| 2002/0012998 | A1 | 1/2002 | Gonda et al. |
| 2002/0041898 | A1* | 4/2002 | Unger et al. .................. 424/486 |
| 2003/0064094 | A1 | 4/2003 | Frankenberger et al. |
| 2003/0161791 | A1 | 8/2003 | Bentley et al. |
| 2003/0211143 | A1 | 11/2003 | Liu et al. |
| 2004/0028682 | A1 | 2/2004 | Border et al. |
| 2006/0074041 | A1 | 4/2006 | Johnston et al. |

FOREIGN PATENT DOCUMENTS

| | | |
|---|---|---|
| JP | 11-269076 | 10/1999 |
| JP | 2002-47211 | 2/2002 |
| JP | 2002-363094 | 12/2002 |
| JP | 2002-371006 | 12/2002 |
| JP | 2003-219893 | 8/2003 |
| JP | 2003/528131 | 9/2003 |
| WO | WO 00/64478 | 11/2000 |
| WO | WO 03/009881 | 2/2003 |
| WO | WO 2004/019921 | 3/2004 |
| WO | WO 2004/069159 | 8/2004 |
| WO | WO 2005/082402 | 9/2005 |

OTHER PUBLICATIONS

Benedetti, A. et al., "Inhibition of the Na+/H+ Exchanger Reduces Rat Hepatic Stellate Cell Activity and Liver Fibrosis: An In Vitro and In Vivo Study," *Gastroenterology* Feb. 2001; 120(2):545-56.

Blomhoff, R. et al., "Newly Administered eH] Retinol is Transferred from Hepatocytes to Stellate Cells in Liver for Storage," *Experimental Cell Research* 1984; 150:186-193.

Blomhoff, R. et al., "Hepatic Uptake of [$^3$H] Retinol Bound to the Serum Retinol Biding Protein Involves Both Parenchmal and Perisinusoidal Stellate Cells," The Journal of Biological Chemistry 1985; 260(25): 13571-13575.

Chansri et al., "Inhibition of liver metastasis by all-*trans* retinoic acid incorporated into O/W emulsions in mice." International Journal of Pharmaceutics. 321:42-49. (2006).

Dixon et al., "*Nonmenclature of Retinoids.*" Pure & Appl. Chem., vol. 55, No. 4, pp. 721-726 (1983).

Dunham et al., "Membrane fusion: Studies with a calcium-sensitive dye, arsenazo III, in liposomes." Proceedings of the National Academy of Science, USA, vol. 74 No. Apr. 4, 1977, pp. 1580-1584.

Elbashir, S.M. et al., "Duplexes of 21-nucleotide RNAs mediate RNA interference in cultured mammalian cells," *Nature* 2001; 411:494-498.

ER Andrew, B Peplinska. "Molecular motion in solid all-trans retinoic acid (vitamin A acid) by proton NMR." Solid State Nuclear, Magnetic Resonance 13, 1998, pp. 39-43.

Extended Search Report dated Jul. 7, 2011 for European Application No. 05819552.0, filed Jul. 18, 2007.

Fallowfield, J.A. et al., "Targeted treatment for cirrhosis," *Expert Opinion Ther Targets* Oct. 2004; 8(5):423-35.

Fire, A. et al., "Potent and specific genetic interference by double-stranded RNA in *Caenorhabditis elegans*," *Nature* 1998; 391:806-811.

Fortuna V.A. et al., "Hepatic Stellate Cells Uptake of Retinol Associated With Retinol-Binding Protein or With Bovine Serum Albumin," *Journal of Cellular Biochemistry* 2003; 90(4):792-805.

Fortunati et al., "A multi-domain protein for β1 integrin-targeted DNA delivery." Gene Therapy. 7:1505-1515. (2000).

Fuja, T.J. et al., "Trans differentiation of vocal-fold stellate cells and *all-trans* retinol-induced deactivation," *Cell Tissue Res.* 2005; 322(3):417-24.

George, J. et al., "In vivo inhibition of rat stellate cell activation by soluble transforming growth factor p type II receptor: A potential new therapy for hepatic fibrosis," *Proc. Natl. Acad. Sci. USA* Oct. 26, 1999; 96(22):12719-24.

Geubel et al., *Gastroenterology* Jun. 1991; 1 00(6): 170 1-9, p. 1701.

Goodman et al., "Extraction and Recombination Studies of the Interaction of Retinol with Human Plasma Retinol-Binding Protein." Journal of Lipid Research, Vo. 13, 1972, pp. 338-347.

Hagiwara, S. et al., "Inhibition of type I procollagen production by tRA va CTE-HSP 47 ribozyme," *J Gene Med.* 2003; 5:784-94.

Hwang et al., "Phospholipid-based microemulsion formulation of all-*trans*-retinoic acid for parenteral administration." International Journal of Pharmaceutics. 276:175-183. (2004).

Iimuro, Y. et al., "Delivery of Matrix Metalloproteinase-1 Attenuates Established Liver Fibrosis in the Rat," *Gastroenterology* 2003; 124:445-458.

Jaster, R., "Molecular regulation of pancreatic stellate cell function," *Molecular Cancer* Oct. 6, 2004; 3(1):26.

Jezequel, A.M. et al., A morphological study of the early stages of hepatic fibrosis induced by low doses of dimentylnitrosame in the rat, *J. Hepatol.* Oct. 1978; 5(2): 174-81.

JX Kang, Y Li, A Leaf. "Mannose-6-phosphateyinsulin-like growth factor-II receptor is a receptor for retinoic acid."Proc. Natl., Acad. Sci., vol. 95, pp. 13671-13676, Dec. 1998.

Kamps, J.A.A.M. et al., "Massive targeting ofliposomes, surface-modified with anionized albumins, to hepatic endothelial cells," *Proceedings of the National Academy of Sciences USA* 1997; 94(21):11681-11685.

Kikuchi, H., Liposomes based on nanotechnology. Past, present and future. Part II, Pharm Tech Japan 2003; 19(3):419-433.

Kim et al., "Folate-tethered emulsion for the target delivery of retinoids to cancer cells." European Journal of Pharmaceutics and Biopharmaceutics. 68:618-625. (2008).

Kircheis et al., "Tumor targeting with surface-shielded ligand-polycation DNA complexes." Journal of Controlled Release. 72:165-170. (2001).

L Beljaars, G Molema, H Bonnema, P Olinga, GMM Groothuis, DKF Meijer, K Poelstra. "Albumin Modified With Mannose 6-Phosphate: A Potential Carrier for Selective Delivery of Antifibrotic Drugs to Rat and Human Hepatic Stellate Cells." Hepatologyvol. 29, No. 5, 1999, pp. 1486-1493.

Landen et al., *Cancer Res.* Aug. 1, 2005; 65(15):6910-8, p. 6911.

Li et al., "Transferrin/Transferrin Receptor-Mediated Drug Delivery." Medicinal Research Reviews. 22(3):225-253. (2002).

Li, D. et al., "Liver fibrogenesis and the role of hepatic stellate cells: New insights and prospects for therapy," *Journal of Gastroenterology and Hepatology* 1999; 14(7):618-633.

Lid, W.B. et al, "Inhibition on the production of collagen type I, III of activated hepatic stellate cells by antisense TIMP-1 recombinant plasmid," *World J. Gastroenterol.* Feb. 2003; 9(2):316-9.

Lim et al., "Formulation parameters determining the physicochemical characteristics of solid lipid nanoparticles loaded with all-trans retinoic acid." International Journal of Pharmaceutics. 243:135-146. (2002).

Liu, X.J. et al., "Effects of the tyrosine protein kinase inhibitor genistein on the proliferation, activation of cultured rat hepatic stellate cells," *World J. Gastroenterol.* Aug. 2002; 8(4):739-45.

Ma et al., "Comparison of Stability for All-*trans* Retinoic Acid Nanosuspensions and Lipid Nanoparticle Formulations." International Conference on Complex Medical Engineering. 197-202. (2007).

Madro, A. et al., "The role of pancreatic stellate cells and cytokines in the development of chronic pancreatitis," *Med. Sci. Monit.* 2004; 10(7):RA166-70.

Marcucci et al., "Active targeting with particulate drug carriers in tumor therapy: fundamentals and recent progress." Drug Discovery Today. 9(5):219-228. (2004).

Marra, F. et al., "Ligands of Peroxisome Proliferator-Activated Receptor y Modulate Profibrogenic and pro inflammatory Actions in Hepatic Stellate Cells," *Gastroenterology* Aug. 2000; 119(2):466-78.

McCaffery et al., "RNA interference in adult mice," *Nature* Jul. 4, 2002; 418(6893):38-9.

Nastruzzi et al., "Liposome-associated retinoic acid increased in vitro antiproliferative effects on neoplastic cells" FEBS Letters (1990) 259(2):293-296.

Office Action dated Apr. 13, 2011 for Philippines Patent Application No. 1-2007-501568, filed Dec. 22, 2005.

Office Action dated Jun. 9, 2011 for Indian Patent Application No. 1094/MUMNP/2007, filed Jul. 23, 2007.

Office Action dated May 9, 2011 for Australian Patent Application No. 2005320014, filed Dec. 22, 2005.

Office Action dated Nov. 9, 2011 for European Application No. 05819552.0.

Office Action dated Oct. 25, 2011 for Indian Patent Application No. 1094/MUMNP/2007, filed Oct. 12, 2011.

Orr, LG. et al., "Mechanism of Action of the Antifibrogenic Compound Gliotoxin in Rat Liver Cells," *Hepatology* Jul. 2004; 40(1):232-42.

Pappo et al., "Monoclonal antibody-directed targeting of fluorescent polystyrene microspheres to Peyer's patch M cells." Immunology. 73:277-280. (1991).

Peterkofsky et al., "Use of a Mixture of Proteinase-Free Collagenases for the Specific Assay of Radioactive Collagen in the Presence of Other Proteins," *Biochemistry* Mar. 16, 1971; 10(6):988-94.

Pinzani, M. et al., "Liver fibrosis: from the bench to clinical targets," *Dig. Liver Dis.* Apr. 2004; 36(4):231-42.

Qi, Z. et al., "Blockade of type p transforming growth factor signaling prevents liver fibrosis and dysfunction in the rat," *Proc. Natl. Acad. Sci. USA* Mar. 2, 1999; 96(5):2345-9.

Rees, J.L. et al., *Biochem J.* May 1, 1989; 259(3):917-9, p. 918.

Sakaida et al., "Fibrosis Accelerates the Development of Enzyme-Altered Lesions in the Rat Liver," *Hepatology* Nov. 1998; 28:1247-1252.

Sasaki, H. et al., "Induction of Heat Shock Protein 47 Synthesis by TGF-p and IL-1P Via Enhancement of the Heat Shock Element Binding Activity of Heat Shock Transcription Factor 1," *The Journal of Immunology* 2002; 168:5178-5183.

Sato et al, "Resolution of liver cirrhosis using vitamin A-coupled liposomes to deliver siRNA against a collagen-specific chaperone", Nature Biotechnology (2008) 26(4):431-442, and supporting information.

Sioud, M. et al., *Biochem Biophys Res Commun* Dec. 26, 2003; 312(4):1220-5, p. 1221.

SR Wassail, W Stillwell. "Retinoid-Phospholipid Interactions as Studied by Magnetic Resonance" Bulletin of Magnetic Resonance, vol. 9 No. 3, 1987, pp. 85-89.

Takahashi et al., "Effects on M5076-Heptatic Metastasis of Retinoic Acid and N-(4-Hydroxyphenyl)Retinamide, Fenretinide Entrapped in SG-Liposomes", Bio. Pharm. Bull. (2003) 26(7):1060-1063.

Torchilin et al., "Immunomicelles: Targeted pharmaceutical carriers for poorly soluble drugs." PNAS. 100(10):6039-6044. (2003).

Torchilin, "Drug Targeting." European Journal of Pharmaceutical Sciences. 11(2):S81-S91. (2000).

Tsuji, H. et al., "Targeting ofliposomes surface-modified with glycyrrhizin to the liver. I. Preparation and biological disposition," *Chemical & Pharmaceutical Bulletin* 1991; 39(4):1004-1008.

Ueki, K. et al., "Hepatocyte growth factor gene therapy of liver cirrhosis in rats," *Nat. Med* Feb. 1999; 5(2):226-30.

Ui-Tei, K. et al., "Sensitive assay of RNA interference in *Drosphila* and Chinese hamster cultured cells using firefly luciferase gene as target," *FEBS Letters* 2000; 479:79-82.

Viguera et al., "A Water-soluble Polylysine-Retinalddehyde Schiff Base." The Journal of Bilogical Chemistry. 265(5): 2527-2532. (1990).

Wang, L. et al., "Effects of herbal compound 861 on human hepatic stellate cell proliferation and activation," *World J. Gastroentero!* Oct. 1, 2004; 10(19):2831-2835.

Whitmer et al., "Membrane-membrane interactions associated with rapid transfer of liposomal bilirubin to microsomal UDP-glucuronyltransferase." Biochemical Jounal, Vo. 244, 1987, pp. 41-47.

Winter et al., "Molecular Imaging of Angiogenesis in Nascent Vx-2 Rabbit Tumors Using a Novel $\alpha v\beta 3$-targeted Nanoparticle and 1.5 Tesla Magnetic Resonance Imaging." Cancer Research. 63:5838-5843. (2003).

Wu, J. et al., "Modification ofliposomes for liver targeting," *Journal ofHepatology* 1996; 24(6):757-763.

Yoshiji, H. et al., "Angiotensin-II type 1 Receptor Interaction Is a Major Regulator for Liver Fibrosis Development in Rats," *Hepatology* Oct. 2001; 34(4 Pt 1):745-50.

Zimmermann, Tracy S. et al, *Nature* May 4, 2006; 441(7089):111-4, p. 111 and p. 113.

Vogel et al., "*An immortalized rat liver stellate cell line (HSC-TS): a new cell model for the study of retinoid metabolism in vitro.*" Journal of Lipid Research, vol. 41, 2000, pp. 882-893.

Office Action issued by the Indian Patent Office dated Feb. 17, 2012 in the corresponding Patent Application No. 1094/MUMNP/2007.

* cited by examiner

Azan staining, 6 random positions imaged

Measured by picking up blue collagen area using NIH Image

DRUG CARRIER AND DRUG CARRIER KIT FOR INHIBITING FIBROSIS

RELATED APPLICATIONS

This application is a divisional of U.S. Ser. No. 11/793,736, filed Apr. 8, 2008, which is a national stage filing under 35 U.S.C. §371 of international application PCT/JP2005/023619, filed Dec. 22, 2005, the disclosures of which are hereby incorporated by reference.

SEQUENCE LISTING

The present application is being filed along with a Sequence Listing in electronic format. The Sequence Listing is provided as a file entitled KUZU1_SEQ.TXT, created Sep. 29, 2011, which is 4 KB in size. The information in the electronic format of the Sequence Listing is incorporated herein by reference in its entirety.

BACKGROUND OF THE INVENTION

1. Field of the Invention

The present invention relates to a drug carrier used in a drug delivery system (DDS) for stellate cells, a medicine containing same, and a kit for preparing said medicine and, in particular, to a medicine and a kit for preparing same wherein an active ingredient is a drug for controlling the activity or growth of stellate cells, and especially a drug targeted at an extracellular matrix constituent molecule secreted by stellate cells, or at one or more molecules having the function of producing or secreting an extracellular matrix constituent molecule.

2. Description of the Related Art

Fibrosis of the liver is caused by, though not limited to, hepatic stellate cells (HSC) being activated as a result of, for example, viral hepatic disease due to hepatitis B or C virus, nonalcoholic steatohepatitis, malnutrition-related diabetes, parasites, infectious diseases such as tuberculosis or syphilis, intrahepatic congestion due to heart disease, or wound healing of tissue injury, etc. inside the liver accompanying a disorder in the passage of bile, etc., and the excessively produced and secreted extracellular matrix (ECM) such as a plurality of types of collagen molecules and fibronectin being deposited on interstitial tissue. The final stage of hepatic fibrosis is hepatic cirrhosis, and since hepatic failure, hepatocellular carcinoma, etc. are caused, in order to prevent them and/or inhibit the progress thereof, there is a desire for the development of a drug carrier and drug carrier kit for inhibiting at least hepatic fibrosis.

Furthermore, in the pancreas, chronic pancreatitis develops as a result of pancreatic fibrosis by the same mechanism as that for hepatic fibrosis (Madro A et al., Med Sci Monit. 2004 July; 10(7): RA166-70.; Jaster R, Mol Cancer. 2004 Oct. 6; 3(1): 26.). However, effective means for inhibiting the progress of pancreatic fibrosis or chronic pancreatitis has not yet been found.

As effective means for inhibiting fibrosis of the liver or the pancreas, there is a possibility that stellate cells are one of the important target candidates (Fallowfield J A, Iredale J P, Expert Opin Ther Targets. 2004 October; 8(5): 423-35; Pinzani M, Rombouts K. Dig Liver Dis. 2004 April; 36(4): 231-42.). In the process of fibrosis, stellate cells are activated by cytokine from Kupffer cells or infiltrating cells and transformed into activated cells, and there is marked production of extracellular matrix (ECM). Stellate cells are known as storage cells for vitamin A, and belong to the myofibroblast family. On the other hand, stellate cells produce matrix metalloproteinase (MMP), its inhibitory factor (TIMP), a cytokine such as TGF-β or PDGF, and a growth factor such as HGF, and play a main role in hepatic fibrosis. Activated stellate cells increase contractile ability and are involved in the regulation of blood flow and, furthermore, they increase the expression of various types of cytokine receptors and become highly sensitive to cytokine.

With regard to therapeutic methods for fibrosis that have been attempted up to the present date, the control of collagen metabolism, promotion of the collagen degradation system, inhibition of activation of stellate cells, etc. can be cited. They include inhibition of TGFβ (known as a factor for activating stellate cells and promoting the production of extracellular matrix (ECM)) using a truncated TGFβ type II receptor (Qi Z et al., Proc Natl Acad Sci USA. 1999 Mar. 2; 96(5): 2345-9.), a soluble TGFβ type II receptor (George J et al., Proc Natl Acad Sci USA. 1999 Oct. 26; 96(22): 12719-24.), HGF (published Japanese translation 5-503076 of a PCT application; Ueki K et al., Nat Med. 1999 February; 5(2): 226-30.), etc., promotion of the production of matrix metalloproteinase (MMP) by means of HGF or an MMP gene-containing vector (Iimuro Y et al., Gastroenterology 2003; 124: 445-458.), inhibition of TIMP, which is an MMP inhibitor, by means of antisense RNA, etc. (Liu W B et al., World J Gastroenterol. 2003 February; 9(2): 316-9), control of the activation of stellate cells by means of a PPARγ ligand (Marra F et al., Gastroenterology. 2000 August; 119(2): 466-78) or an angiotensin-II type I receptor antagonist (Yoshiji H et al., Hepatology. 2001 October; 34 (4 Pt 1): 745-50.), inhibition of the growth of stellate cells via inhibition of PDGF action by means of PDGF tyrosine kinase inhibitor, etc. (Liu X J et al., World J Gastroenterol. 2002 August; 8(4): 739-45.) and inhibition of the sodium channel by means of amiloride (Benedetti A et al., Gastroenterology. 2001 February; 120(2): 545-56), etc., and apoptotic induction of stellate cells by means of Compound 861 (Wang L, et al., World J Gastroenterol 2004 Oct. 1; 10(19): 2831-2835), gliotoxin (Orr J G et al., Hepatology. 2004 July; 40(1): 232-42.), etc. However, in all cases, since the specificity of action and/or the organ specificity are low, there are problems with the effects and with side effects.

With regard to collagen protein synthesis, there are many unclear points with respect to the metabolic route, and a therapeutic method using a drug that inhibits this has not been established as a therapeutic method that is efficient and safe toward a living body in terms of side effects. That is, in a method in which molecules involved in the production of collagen are targeted, the specificity for the target cannot be enhanced because of the diversity of function of the molecules, and the possibility of causing side effects is high. If collagen, which is the final product, could be inhibited directly, this would be reasonable as a common therapeutic method for fibrosis processes, and in order to do this it would be necessary to control all the various types of collagen represented by Types I to IV at the same time.

As effective means for controlling synthesis of various types of collagen molecules simultaneously without losing specificity to collagen, a method for controlling the function of HSP47 can be considered. HSP47 is a collagen-specific molecular chaperone that is essential for intracellular transport and molecular maturation, which are common to synthetic processes for various types of collagen. Therefore, if in stellate cells the function of HSP47 can be controlled specifically, there is a possibility of inhibiting hepatic fibrosis, but there are no reports of such a therapeutic method being attempted.

The present inventors prepared a ribozyme that specifically controls the function of HSP47 in a cellular system, and showed that the production and secretion of collagens can be controlled by the ribozyme at the same time (Sasaki H, et al. Journal of Immunology, 2002, 168: 5178-83; Hagiwara S, et al. J Gene Med. 2003, 5: 784-94). In order to specifically control the synthesis of HSP47, siRNA, which is easier to optimize than ribozyme, can be employed. The siRNA (small interfering RNAs) used in the present specification is a general term for double-strand RNA used in RNAi (RNA interference). RNAi is a phenomenon in which double-strand RNA (double-strand RNA; dsRNA), which is formed from sense RNA and antisense RNA and is homologous with a given gene, destroys a homologous segment of a transcript (mRNA) of the gene. It was originally exhibited in an experiment using a nematode (Fire A, et al: Nature (1998) 391: 806-811), and it has been shown that a similar induction mechanism is present in mammalian cells (Ui-Tei K, et al: FEBS Lett (2000) 479: 79-82). Furthermore, Elbashir et al. have shown that a short dsRNA having a length of on the order of 21 to 23 by can induce RNAi in a mammalian cell system without exhibiting cytotoxicity (Elbashir S M, et al: Nature (2001) 411: 494-498). However, in order for the effects of these molecules to be exhibited effectively, it is necessary to employ a method that is specific to a target organ.

[Patent Publication 1] Japanese translation 5-503076 of a PCT application

[Nonpatent Publication 1] Madro A et al., Med Sci Monit. 2004 July; 10(7): RA166-70

[Nonpatent Publication 2] Jaster R, Mol Cancer. 2004 Oct. 6; 3(1): 26

[Nonpatent Publication 3] Fallowfield J A, Iredale J P, Expert Opin Ther Targets. 2004 October; 8(5): 423-35

[Nonpatent Publication 4] Pinzani M, Rombouts K. Dig Liver Dis. 2004 April; 36(4): 231-42

[Nonpatent Publication 5] Qi Z et al., Proc Natl Acad Sci USA. 1999 Mar. 2; 96(5): 2345-9

[Nonpatent Publication 6] George J et al., Proc Natl Acad Sci USA. 1999 Oct. 26; 96(22): 12719-24

[Nonpatent Publication 7] Ueki K et al., Nat Med. 1999 February; 5(2): 226-30

[Nonpatent Publication 8] Iimuro Y et al., Gastroenterology 2003; 124: 445-458

[Nonpatent Publication 9] Liu W B et al., World J Gastroenterol. 2003 February; 9(2): 316-9

[Nonpatent Publication 10] Marra F et al., Gastroenterology. 2000 August; 119(2): 466-78

[Nonpatent Publication 11] Yoshiji H et al., Hepatology. 2001 October; 34(4 Pt 1): 745-50

[Nonpatent Publication 12] Liu X J et al., World J Gastroenterol. 2002 August; 8(4): 739-45

[Nonpatent Publication 13] Benedetti A et al., Gastroenterology. 2001 February; 120(2): 545-56

[Nonpatent Publication 14] Wang L et al., World J Gastroenterol 2004 Oct. 1; 10(19): 2831-2835

[Nonpatent Publication 15] Orr J G et al., Hepatology. 2004 July; 40(1): 232-42

[Nonpatent Publication 16] Sasaki H et al., Journal of Immunology, 2002, 168: 5178-83

[Nonpatent Publication 17] Hagiwara S et al., J Gene Med. 2003, 5: 784-94

[Nonpatent Publication 18] Fire A et al.: Nature (1998) 391: 806-811

[Nonpatent Publication 19] Ui-Tei K et al.: FEBS Lett (2000) 479: 79-82

[Nonpatent Publication 20] Elbashir S M et al.: Nature (2001) 411: 494-498

[Nonpatent Publication 21] Yasuhiko Tabata, New Developments in Drug Delivery System DDS Technology and their Application—Cutting-edge technology for biomedical research and advanced medical treatment, Medical Do, ISBN: 4944157932, 2003

[Nonpatent Publication 22] Mitsuru Hashida, Drug Delivery Systems—New challenges for drug discovery and therapy, New Bioscience Series, Kagaku-dojin, ISBN: 4759803858, 1995

SUMMARY OF THE INVENTION

Problems to be Solved by the Invention

In order to target a tissue and/or an organ, the application of a drug delivery system (DDS) is one effective means (Yasuhiko Tabata, New Developments in Drug Delivery System DDS Technology and their Application—Cutting-edge technology for biomedical research and advanced medical treatment, Medical Do, ISBN: 4944157932, 2003: Mitsuru Hashida, Drug Delivery Systems—New challenges for drug discovery and therapy, New Bioscience Series, Kagaku-dojin, ISBN: 4759803858, 1995). As a drug carrier used in the drug delivery system (DDS), there are those in which a polymer micelle, a liposome, a microemulsion, etc. is applied. As a technique for enhancing the specificity of these carriers toward a target organ, there are known a technique in which an antibody and/or ligand for an organ- and/or tissue-specific antigen or receptor is mixed with or bonded to the carrier, and a technique in which physicochemical properties of the carrier are utilized, but there is no known technique for the particular case in which stellate cells are targeted.

Means for Solving the Problems

The present invention relates to a drug carrier and a drug carrier kit that enable a diagnostic and/or therapeutic drug to be specifically transported to stellate cells. The drug carrier in the present invention may be in any of polymer micelle, liposome, emulsion, microsphere, and nanosphere form, and by bonding thereto or including therein vitamin A (VA), a retinoid derivative such as, for example, tretinoin, adapalene, or retinol palmitate, or a vitamin A analogue such as, for example, Fenretinide (4-HPR), a therapeutic drug can be transported specifically to hepatic stellate cells. Furthermore, by preparing one in which the drug carrier includes one molecule or a plurality of molecules selected from TGFβ activity inhibitors such as a truncated TGFβ type II receptor and a soluble TGFβ type II receptor, growth factor preparations such as HGF, MMP production promoters such as an MMP gene-containing adenovirus vector, a cell activation inhibitors and/or growth inhibitors including a PPARγ-ligand, an angiotensin-II type I receptor antagonist, a PDGF tyrosine kinase inhibitor, and a sodium channel inhibitor such as amiloride, and apoptosis inducers such as compound 861 and gliotoxin, and by orally, or parenterally, for example, intravenously or intraperitoneally administering it to a patient having a risk of fibrosis or fibrosis symptoms, or patients having various fibrosis-related disorders such as, for example, hepatic cirrhosis, hepatic failure, liver cancer, or chronic pancreatitis, the activation of stellate cells can be suppressed, and fibrosis and/or fibrosis-related disease conditions can be prevented, inhibited, or improved. Alternatively, or in addition thereto, by using the drug carrier which encloses therein a ribozyme, an antisense RNA, or an siRNA that specifically inhibits HSP47, which is a collagen-specific molecular chaperone, or TIMP, which is an MMP inhibitor, secretion of type I to IV collagens can be inhibited simultaneously, and as a result fibrogenesis can be inhibited effectively.

Therefore, the present invention relates to a stellate cell-specific drug carrier having a retinoid derivative and/or a vitamin A analogue as a component.

Furthermore, the present invention relates to the drug carrier wherein the retinoid derivative includes vitamin A.

Moreover, the present invention relates to the drug carrier wherein the retinoid derivative and/or the vitamin A analogue are contained at 0.2 to 20 wt %.

Furthermore, the present invention relates to the drug carrier wherein it is in any one of polymer micelle, liposome, emulsion, microsphere, and nanosphere form.

Moreover, the present invention relates to a medicine for treating a stellate cell-related disorder, the medicine including the drug carrier and a drug for controlling the activity or growth of stellate cells.

Furthermore, the present invention relates to the medicine wherein the disorder is selected from the group consisting of hepatitis, hepatic fibrosis, hepatic cirrhosis, liver cancer, pancreatitis, pancreatic fibrosis, pancreatic cancer, vocal cord scarring, vocal cord mucosal fibrosis, and laryngeal fibrosis.

Moreover, the present invention relates to the medicine wherein the drug for controlling the activity or growth of stellate cells is selected from the group consisting of a TGFβ activity inhibitor, a preparation having HGF activity, an MMP production promoter, a TIMP production inhibitor, a PPARγ ligand, an angiotensin activity inhibitor, a PDGF activity inhibitor, a sodium channel inhibitor, an apoptosis inducer, and an siRNA, ribozyme, antisense nucleic acid, or DNA/RNA chimera polynucleotide, or a vector expressing same, that targets an extracellular matrix constituent molecule produced by stellate cells or one or more molecules having the function of producing or secreting the extracellular matrix constituent molecule.

Furthermore, the present invention relates to the medicine wherein the molecule having the function of producing or secreting the extracellular matrix constituent molecule is HSP47.

Moreover, the present invention relates to the medicine wherein the drug and the drug carrier are mixed at a place of medical treatment or in the vicinity thereof Furthermore, the present invention relates to a preparation kit for the medicine, the kit including one or more containers containing one or more of the drug for controlling the activity or growth of stellate cells, a drug carrier constituent, and a retinoid derivative and/or a vitamin A analogue.

Moreover, the present invention relates to a method for treating a stellate cell-related disorder, the method including administering an effective amount of the medicine to a subject in need thereof Furthermore, the present invention relates to the method wherein the disorder is selected from the group consisting of hepatitis, hepatic fibrosis, hepatic cirrhosis, liver cancer, pancreatitis, pancreatic fibrosis, pancreatic cancer, vocal cord scarring, vocal cord mucosal fibrosis, and laryngeal fibrosis.

Moreover, the present invention relates to the method wherein the medicine is parenterally administered.

Furthermore, the present invention relates to use of the drug carrier in the production of a medicine for treating a stellate cell-related disorder.

Moreover, the present invention relates to a drug delivery method for stellate cells utilizing the drug carrier.

Furthermore, the present invention also relates to a drug carrier for inhibiting fibrosis that includes a retinoid derivative and/or a vitamin A analogue as a component and transports a drug for controlling the activity or growth of stellate cells specifically to stellate cells, the drug carrier for inhibiting fibrosis wherein the retinoid derivative includes vitamin A, the drug carrier for inhibiting fibrosis wherein the retinoid derivative and/or the vitamin A analogue are contained at 0.2% to 20%, the drug carrier for inhibiting fibrosis wherein it is in any one of polymer micelle, liposome, emulsion, microsphere, and nanosphere form, the drug carrier for inhibiting fibrosis wherein the drug for controlling the activity or growth of stellate cells includes one or more drugs selected from a TGFβ activity inhibitor, a preparation having HGF activity, an MMP production promoter, a TIMP production inhibitor, a PPARγ ligand, an angiotensin activity inhibitor, a PDGF activity inhibitor, a sodium channel inhibitor, and an apoptosis inducer, the drug carrier for inhibiting fibrosis wherein the drug for controlling the activity or growth of stellate cells includes an siRNA, a ribozyme, or an antisense RNA, or a vector expressing same, that targets an extracellular matrix constituent molecule produced by stellate cells, or that targets one or more molecules having the function of producing or secreting the extracellular matrix constituent molecule, and the drug carrier for inhibiting fibrosis wherein the molecule having the function of producing or secreting the extracellular matrix constituent molecule is HSP47.

Moreover, the present invention relates to a drug carrier kit for inhibiting fibrosis that includes one or more containers containing one or more of a drug for controlling the activity or growth of stellate cells, a drug carrier constituent, and a retinoid derivative and/or a vitamin A analogue, the drug carrier kit for inhibiting fibrosis wherein the retinoid derivative includes vitamin A, the drug carrier kit for inhibiting fibrosis wherein the retinoid derivative and/or the vitamin A analogue are contained at 0.2% to 20%, the drug carrier kit for inhibiting fibrosis wherein it is in any one of polymer micelle, liposome, emulsion, microsphere, and nanosphere form, the drug carrier kit for inhibiting fibrosis wherein the drug for controlling the activity or growth of stellate cells includes one or more drugs selected from a TGFβ activity inhibitor, a preparation having HGF activity, an MMP production promoter, a TIMP production inhibitor, a PPARγ ligand, an angiotensin activity inhibitor, a PDGF activity inhibitor, a sodium channel inhibitor, and an apoptosis inducer, the drug carrier kit for inhibiting fibrosis wherein the drug for controlling the activity or growth of stellate cells includes an siRNA, a ribozyme, or an antisense RNA, or a vector expressing same, that targets an extracellular matrix constituent molecule secreted by stellate cells, or that targets one or more molecules having the function of producing or secreting the extracellular matrix constituent molecule, and the drug carrier kit for inhibiting fibrosis wherein the molecule having the function of producing or secreting the extracellular matrix constituent molecule is HSP47.

Effects of the Invention

By the use of the drug carrier and the drug carrier kit of the present invention that enable a diagnostic and/or therapeutic drug to be transported specifically to stellate cells as effective means for preventing, suppressing, or improving fibrosis and/or various types of fibrosis-related disorders, innovative therapeutic effects such as shown by Examples can be provided. That is, since the drug carrier and the drug carrier kit of the present invention specifically target stellate cells, clinical conditions that develop mainly due to stellate cells such as, for example, fibrosis, can be inhibited efficiently and effectively while minimizing side effects.

DETAILED DESCRIPTION OF THE PREFERRED EMBODIMENT

Figure 1:
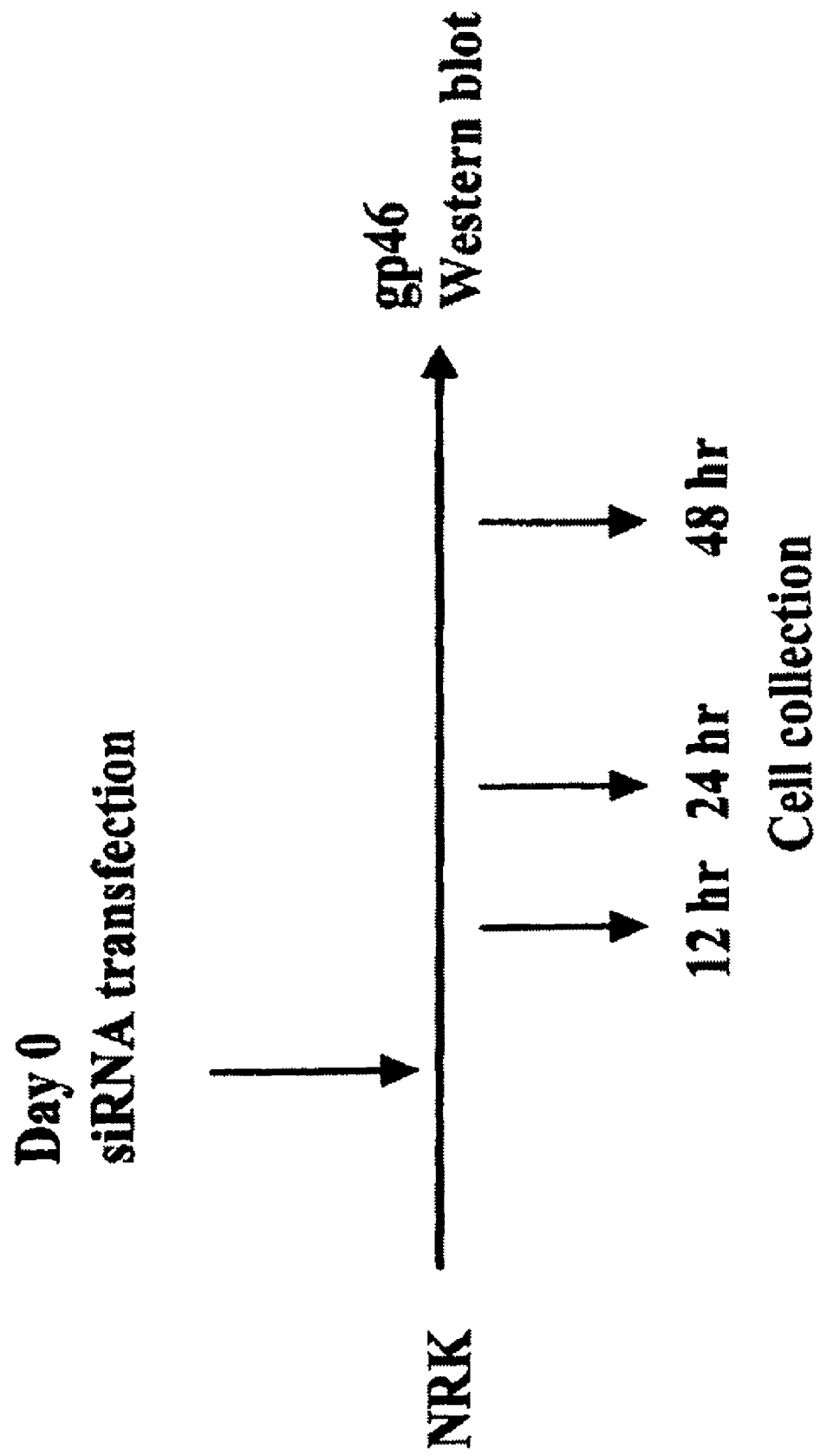
[FIG. 1] A diagram showing a protocol with respect to assessment of the effect of gp46-siRNA in vitro using NRK cells, and determination of optimal sequence, timing, and concentration.

The retinoid derivative and/or vitamin A analogue in the present invention includes vitamin A as well as a retinoid derivative or vitamin A analogue in a state in which it is dissolved in or mixed with a medium that can dissolve or retain it.

Any retinoid derivative and/or vitamin A analogue may be used in the present invention as long as it is actively accumulated by stellate cells; examples of the retinoid derivative include, but are not limited to, tretinoin, adapalene, retinol palmitate, and in particular vitamin A, retinoic acid, and examples of the vitamin A analogue include, but are not limited to, Fenretinide (4-HPR). The present invention utilizes the property of stellate cells to positively incorporate a retinoid derivative and/or a vitamin A analogue, and by using the retinoid derivative and/or vitamin A analogue as a drug carrier or by bonding to or being included in another drug carrier component, a desired material or body is transported specifically to stellate cells.

The drug carrier of the present invention therefore may contain a drug carrier component other than the retinoid derivative and/or vitamin A analogue. Such a component is not particularly limited, and any component known in the fields of medicine and pharmacy may be used, but it is preferable for it to be capable of including the retinoid derivative and/or vitamin A analogue or bonding thereto. Examples of such a component include a lipid, for example, a phospholipid such as glycerophospholipid, a sphingolipid such as sphingomyelin, a sterol such as cholesterol, a vegetable oil such as soybean oil or poppy seed oil, mineral oil, and a lecithin such as egg-yolk lecithin, but the examples are not limited thereto. Among them, those that can form a liposome are preferable, for example, natural phospholipids such as lecithin, semisynthetic phospholipids such as dimyristoylphosphatidylcholine (DMPC), dipalmitoylphosphatidylcholine (DPPC), and distearoylphosphatidylcholine (DSPC), and cholesterol.

Furthermore, the drug carrier of the present invention may contain a substance that improves incorporation into stellate cells, for example, retinol-binding protein (RBP).

The bonding or inclusion of the retinoid derivative and/or vitamin A analogue with the drug carrier of the present invention may also be carried out by bonding or including the retinoid derivative and/or vitamin A analogue with another component of the drug carrier by chemical and/or physical methods. Alternatively, bonding or inclusion of the retinoid derivative and/or vitamin A analogue with the drug carrier of the present invention may also be carried out by mixing the retinoid derivative and/or vitamin A analogue having formation-affinity and basic components of the drug carrier, into the drug carrier components during preparation of the drug carrier. The amount of retinoid derivative and/or vitamin A analogue bonded to or included in the drug carrier of the present invention may be 0.01% to 100% as a ratio by weight relative to the drug carrier components, preferably 0.2% to 20%, and more preferably 1% to 5%.

The drug carrier of the present invention may be in any form as long as a desired material or body can be transported to target stellate cells, and examples of the form include, but are not limited to, polymer micelle, liposome, emulsion, microsphere, and nanosphere. Furthermore, the drug carrier of the present invention may include in its interior the substance that is to be transported, be attached to the exterior of the substance that is to be transported, or be mixed with the substance that is to be transported as long as the retinoid derivative and/or vitamin A analogue included therein is at least partially exposed on the exterior of the preparation before it reaches the stellate cells at the latest.

The drug carrier of the present invention specifically targets stellate cells and enables a desired effect such as, for example, inhibition or prevention of fibrosis to be exhibited with the maximum effect and minimum side effects by efficiently transporting to stellate cells a desired material or body such as, for example, a drug for controlling the activity or growth of stellate cells. The material or body that the present drug carrier delivers is not particularly limited, but it preferably has a size that enables physical movement in a living body from an administration site to the liver, pancreas, etc., where stellate cells are present. The drug carrier of the present invention therefore can transport not only a material such as an atom, a molecule, a compound, a protein, or a nucleic acid but also a body such as a vector, a virus particle, a cell, a drug release system constituted from one or more elements, or a micromachine. The material or body preferably has the property of exerting some effect on stellate cells, and examples thereof include one that labels stellate cells and one that controls the activity or growth of stellate cells.

Therefore, in one embodiment of the present invention, it is a 'drug for controlling the activity or growth of stellate cells' that the drug carrier delivers. This may be any drug that directly or indirectly inhibits the physicochemical actions of stellate cells involved in the promotion of fibrosis, and examples thereof include, but are not limited to, TGFβ activity inhibitors such as a truncated TGFβ type II receptor and a soluble TGFβ type II receptor, growth factor preparations such as HGF and expression vectors therefor, MMP production promoters such as an MMP gene-containing adenovirus vector, TIMP production inhibitors such as an antisense TIMP nucleic acid, a PPARγ ligand, cell activation inhibitors and/or cell growth inhibitors such as an angiotensin activity inhibitor, a PDGF activity inhibitor, and a sodium channel inhibitor, and also apoptosis inducers such as compound 861 and gliotoxin, adiponectin (JP, A, 2002-363094), and a compound having Rho kinase inhibitory activity such as (+)-trans-4-(1-aminoethyl)-1-(4-pyridylcarbamoyl)cyclohexane (WO 00/64478). Furthermore, the 'drug for controlling the activity or growth of stellate cells' in the present invention may be any drug that directly or indirectly promotes the physicochemical actions of stellate cells directly or indirectly involved in the inhibition of fibrosis, and examples thereof include, but are not limited to, a drug for promoting a collagen degradation system, e.g., MMP production promoters such as an MMP expression vector, HGF, and drugs having HGF-like activity such as HGF analogues and expression vectors therefor.

Other examples of the 'drug for controlling the activity or growth of stellate cells' in the present invention include a drug for controlling the metabolism of an extracellular matrix such as collagen, for example, a substance having an effect in inhibiting the expression of a target molecule, such as siRNA, ribozyme, and antisense nucleic acid (including RNA, DNA, PNA, and a composite thereof), a substance having a dominant negative effect, and vectors expressing same, that target, for example, an extracellular matrix constituent molecule produced by stellate cells or target one or more molecules that have the function of producing or secreting the extracellular matrix constituent molecule.

The siRNA is a double-strand RNA having a sequence specific to a target molecule such as an mRNA, and promotes degradation of the target molecule, thus inhibiting expression of a material formed thereby such as, for example, a protein (RNA interference). Since the principle was published by Fire et al. (Nature, 391: 806-811, 1998), a wide range of research has been carried out into the optimization of siRNA, and a person skilled in the art is familiar with such techniques. Furthermore, materials other than siRNA that cause RNA interference or another gene expression inhibition reaction have been intensively investigated, and there are currently a large number of such materials.

For example, JP, A, 2003-219893 describes a double-strand polynucleotide formed from RNA and DNA that inhibits the expression of a target gene. This polynucleotide may be a DNA/RNA hybrid in which one of two strands is DNA and the other is RNA, or a DNA/RNA chimera in which one portion of the same strand is DNA and the other portion is RNA. Such a polynucleotide is preferably formed from 19 to 25 nucleotides, more preferably 19 to 23 nucleotides, and yet more preferably 19 to 21 nucleotides; in the case of the DNA/RNA hybrid, it is preferable that the sense strand is DNA and the antisense strand is RNA, and in the case of the DNA/RNA chimera, it is preferable that one portion on the upstream side of the double-strand polynucleotide is RNA. Such a polynucleotide may be prepared so as to have any sequence in accordance with a chemical synthetic method known per se.

With regard to the target molecule, for example, a molecule that can inhibit the secretion of all extracellular matrix constituent molecules together is preferable, and examples of such a molecule include, but are not limited to, HSP47. HSP47 or a homologous gene sequence thereof is disclosed as, for example, GenBank accession No. AB010273 (human), X60676 (mouse), or M69246 (rat, gp46).

Preferred examples of the material that is transported by the drug carrier of the present invention include an siRNA, a DNA/RNA hybrid or chimera polynucleotide, and an antisense nucleic acid, that targets HSP47.

Examples of a material that is delivered by the drug carrier of the present invention include a drug for inhibiting fibrosis such as, for example, G-CSF (WO 2005/082402), a thrombomodulin-like protein (JP, A, 2002-371006), and keratan sulfate oligosaccharide (JP, A, 11-269076).

The material or body that is delivered by the drug carrier of the present invention may or may not be labeled. Labeling is useful at the testing and research level in particular since the feasibility of transport or an increase or decrease in stellate cells can be monitored. A label may be selected from those known to a person skilled in the art; for example, any radioactive isotope, a material that can bond to a material to be labeled (e.g. an antibody), a fluorescent material, a fluorophore, a chemiluminescent material, and an enzyme.

The present invention also relates to a medicine for treating a stellate cell-related disorder, the medicine containing the drug carrier and the drug for controlling the activity or growth of stellate cells, and relates to the use of the drug carrier in the production of a medicine for treating a stellate cell-related disorder. The stellate cell-related disorder referred to here means a disorder in which stellate cells are directly or indirectly involved in the process of the disorder, that is, the onset, exacerbation, improvement, remission, cure, etc. of the disorder, and examples thereof include hepatic disorders such as hepatitis, in particular chronic hepatitis, hepatic fibrosis, hepatic cirrhosis, and liver cancer, and pancreatic disorders such as pancreatitis, in particular chronic pancreatitis, pancreatic fibrosis, and pancreatic cancer. Furthermore, according to recent reports, since stellate cells are present in the vocal cord (e.g. Fuja T J et al., Cell Tissue Res. 2005; 322(3): 417-24), the above-mentioned disorders include disorders of the vocal cord and larynx such as vocal cord scarring, vocal cord mucosal fibrosis, and laryngeal fibrosis.

In the medicine of the present invention, the drug carrier may include a drug in its interior, be attached to the exterior of a drug-containing substance, or be mixed with a drug as long as the retinoid derivative and/or vitamin A analogue included in the drag carrier is at least partially exposed on the exterior of the preparation before it reaches the stellate cells at the latest. Therefore, depending on the route of administration or manner in which the drug is released, the medicine may be covered with an appropriate material, such as, for example, an enteric coating or a material that disintegrates over time, or may be incorporated into an appropriate drug release system.

The medicine of the present invention may be administered via various types of route including oral and parenteral routes; examples thereof include, but are not limited to, oral, intravenous, intramuscular, subcutaneous, local, rectal, intraarterial, intraportal, intraventricular, transmucosal, percutaneous, intranasal, intraperitoneal, intrapulmonary, and intrauterine routes, and the medicine may be prepared in a form appropriate for each administration route. Such a form and a preparation method may employ any known form and method as appropriate (e.g. 'Hyoujun Yakuzaigaku' (Standard Pharmaceutics), Ed. Y. Watanabe et al., Nankodo, 2003, etc.).

Examples of forms suitable for oral administration include, but are not limited to, powder, granule, tablet, capsule, liquid, suspension, emulsion, gel, and syrup, and examples of forms suitable for parenteral administration include injections such as injectable solution, injectable suspension, injectable emulsion, and an on-site preparation type injection. The formulation for parenteral administration may be in the form of an aqueous or nonaqueous isotonic sterile solution or suspension.

The drug carrier or the medicine of the present invention may be supplied in any configuration, but from the viewpoint of storage stability, it is preferably provided in a configuration that allows on-site preparation, for example, in a configuration that allows a doctor and/or a pharmacist, a nurse, or another paramedic to prepare it at the place of medical treatment or in the vicinity thereof. In this case, the drug carrier or the medicine of the present invention is provided as one or more containers containing at least one essential component therefor, and is prepared prior to use, for example, within 24 hours, preferably within 3 hours, and more preferably immediately prior to use. When carrying out the preparation, a reagent, a solvent, preparation equipment, etc. that are normally available at a place of preparation may be used as appropriate.

The present invention therefore includes a drug carrier or medicine preparation kit containing one or more containers containing one or more of a drug carrier constituent, a retinoid derivative and/or a vitamin A analogue, and/or a drug, and also includes an essential component for the drug carrier or the medicine provided in the form of such a kit. The kit of the present invention may contain, in addition to those described above, a description, etc. in which a preparation method or an administration method for the drug carrier and the medicine of the present invention is described. Furthermore, the kit of the present invention may contain all components for completing the drug carrier or the medicine of the present invention but need not necessarily contain all of the components. The kit of the present invention therefore need not contain a reagent or a solvent that is normally available at a place of medical treatment, an experimental facility, etc. such as, for example, sterile water, saline, or a glucose solution.

The present invention further relates to a method for treating a stellate cell-related disorder, the method including administering an effective amount of the medicine to a subject in need thereof. The effective amount referred to here is an amount that suppresses onset of the target disorder, reduces symptoms thereof, or prevents progression thereof, and is preferably an amount that prevents onset of the target disorder or cures the target disorder. It is also preferably an amount that does not cause an adverse effect that exceeds the benefit from administration. Such an amount may be determined as appropriate by an in vitro test using cultured cells, etc. or by a test in a model animal such as a mouse, a rat, a dog, or a pig, and such test methods are well known to a person skilled in the art.

The dosage of a medicine administered by the method of the present invention depends on the type of drug used or the type of retinoid derivative and/or vitamin A analogue and, for example, when an siRNA for HSP47 is used as the drug, the weight of the drug is, for example, 0.01 to 45 mg/kg/day, preferably 0.1 to 30 mg/kg/day, more preferably 1 to 20 mg/kg/day, and most preferably 4 to 6 mg/kg/day. When vitamin A is used as the retinoid derivative and/or vitamin A analogue, vitamin A is typically administered at a dosage of 10 to 20 mg/kg/day. The retinoid derivative and/or vitamin A analogue contained in the drug carrier and the dosage of the drug used in the method of the present invention are either known to a person skilled in the art or are determined as appropriate by the above-mentioned test, etc.

A specific dosage of a medicine administered in the method of the present invention can be determined while taking into consideration various conditions of a subject that requires treatment, for example, the severity of symptoms, general health conditions of the subject, age, weight, sex of the subject, diet, the timing and frequency of administration, a medicine used in combination, responsiveness to treatment, and compliance with treatment, and it might be different from the above-mentioned typical dosage, but in such a case, these methods are still included in the scope of the present invention.

With regard to the administration route, there are various routes including both oral and parenteral routes such as, for example, oral, intravenous, intramuscular, subcutaneous, local, rectal, intraarterial, intraportal, intraventricular, transmucosal, percutaneous, intranasal, intraperitoneal, intrapulmonary, and intrauterine routes.

The frequency of administration depends on the properties of the medicine used and the above-mentioned conditions of the subject and may be, for example, a plurality of times a day (i.e. 2, 3, 4, 5, or more times per day), once a day, every few days (i.e. every 2, 3, 4, 5, 6, or 7 days, etc.), once a week, or once every few weeks (i.e. once every 2, 3, or 4 weeks, etc.).

In the method of the present invention, the term 'subject' means any living individual, preferably an animal, more preferably a mammal, and yet more preferably a human individual. In the present invention, the subject may be healthy or affected with some disorder, and in the case of treatment of a disorder being intended, the subject typically means a subject affected with the disorder or having a risk of being affected.

Furthermore, the term 'treatment' includes all types of medically acceptable prophylactic and/or therapeutic intervention for the purpose of the cure, temporary remission, prevention, etc. of a disorder. For example, when the disorder is hepatic fibrosis, the term 'treatment' includes medically acceptable intervention for various purposes including delaying or halting the progression of fibrosis, regression or disappearance of lesions, prevention of the onset of fibrosis, or prevention of recurrence.

The present invention also relates to a method for delivering a drug to stellate cells using the drug carrier. This method includes, but is not limited to, a step of supporting a substance to be delivered on the drug carrier, and a step of administering or adding the drug carrier carrying the substance to be delivered to a stellate cell-containing living body or medium, such as, for example, a culture medium. These steps may be achieved as appropriate in accordance with any known method, the method described in the present specification, etc. This delivery method may be combined with another delivery method, for example, another delivery method in which an organ where stellate cells are present is the target, etc.

EXAMPLES

The Examples below are only intended to explain the present invention, and the scope of the present invention is not limited by specific numeric values and procedures shown in the Examples.

Example 1

Preparation of siRNA for gp46

Among optimal sequences for siRNA recognition in targeting a base sequence of HSP47, which is a common molecular chaperone for collagens (types I to IV), Sequences A and B were prepared in accordance with an siRNA oligo design program by iGENE Therapeutics, Inc. Sequence C was prepared by searching on the Internet using the siRNA Target Finder (http://www.ambion.com/techlib/misc/siRNA$_{13}$finder.html) from Ambion, Inc. and selecting 19 base sequences that would become a target for rat gp46 (human HSP47 homologue, GenBank Accession No. M69246). When carrying out the design, care was taken in 1) starting at 75 to 100 bases downstream from the initiation codon, 2) positioning the first AA dimer, and 3) making sure that the GC content was 30% to 70%. In this example, siRNAs having the sequences below were prepared.

```
   (25 base forward direction strand siRNA starting
           at 757th in the sequence, SEQ ID NO: 1)
A: GUUCCACCAUAAGAUGGUAGACAAC (25 base forward direction strand siRNA starting
           at 1626th in the sequence, SEQ ID NO: 2)
B: CCACAAGUUUUAUAUCCAAUCUAGC (19 base forward direction strand siRNA starting
           at 64th in the sequence, SEQ ID NO: 3)
C: GAAACCUGUAGAGGCCGCA
```

Example 2

Inhibition of gp46 Expression by Prepared siRNA

Normal rat kidney cells (NRK cells), which had rat gp46 and were fibroblasts producing collagen, were transfected with 0.1 nM to 50 nM siRNA and cultured for 12 to 48 hours (FIG. 1). The amount of expression of gp46 was checked by the western blot method (FIGS. 2 to 4, upper band corresponding to gp46, lower band corresponding to actin control).

Figure 2:
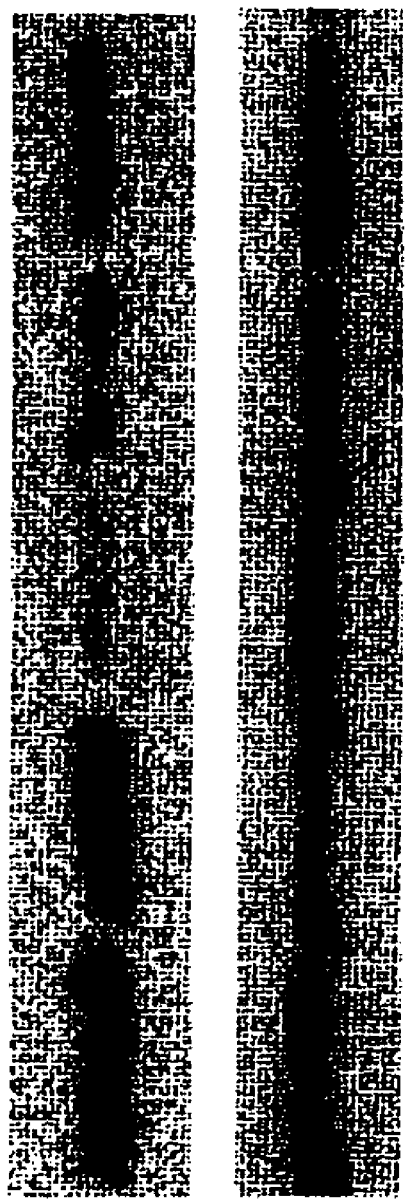
[FIG. 2] A photographic diagram showing the result of western blotting of gp46 and actin (24 hour culturing, examination of optimal sequence).
Figure 3:
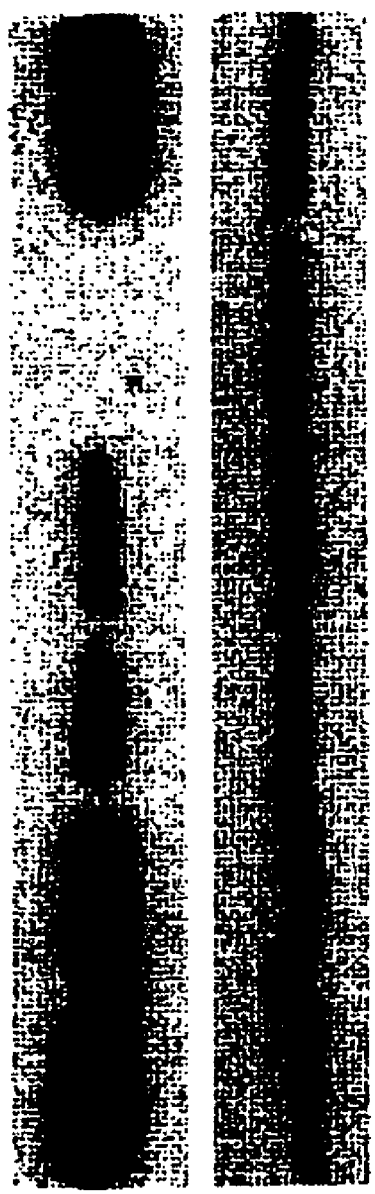
[FIG. 3] A photographic diagram showing the result of western blotting of gp46 and actin (24 hour culturing, examination of optimal concentration).
Figure 4:
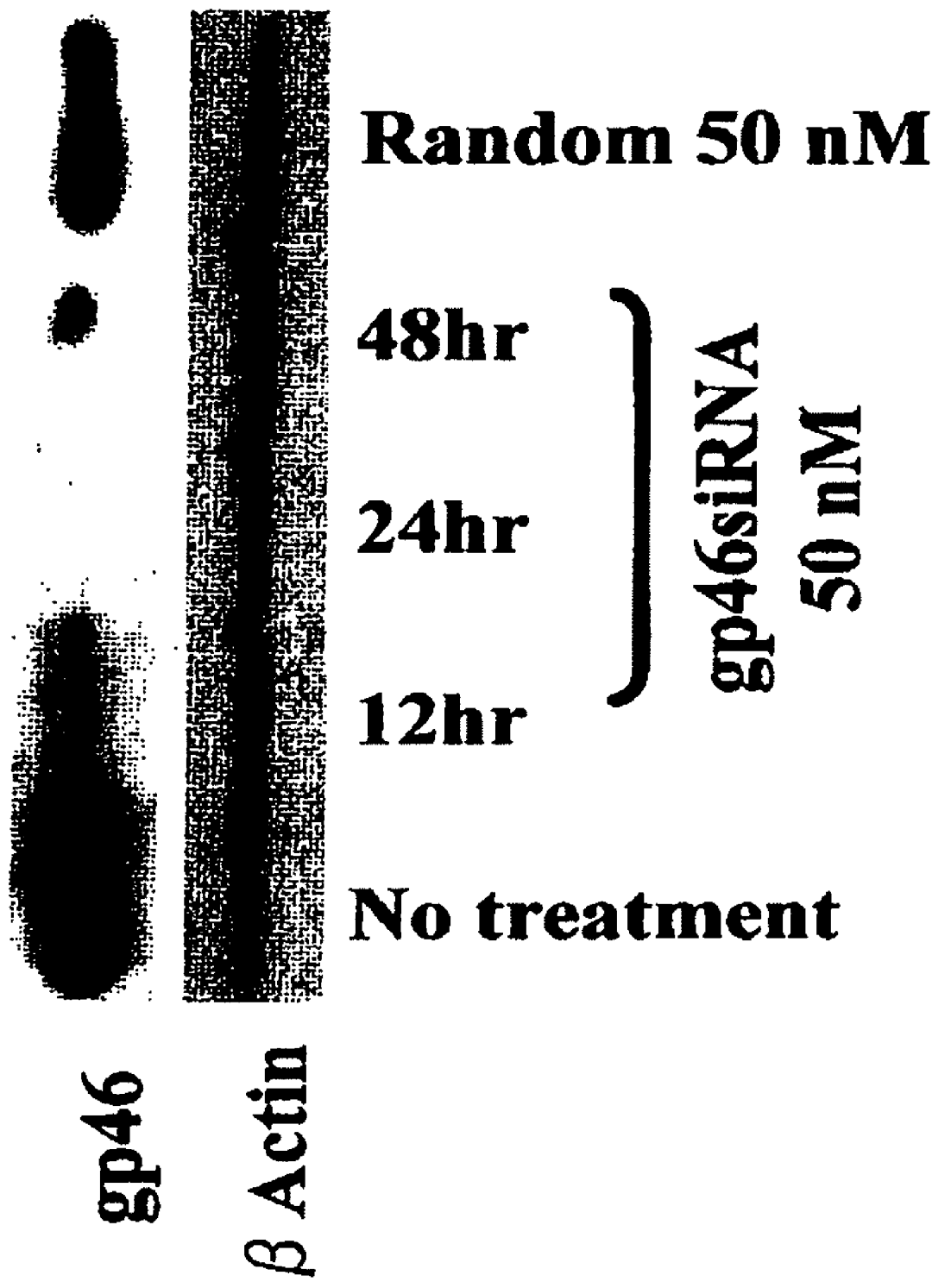
[FIG. 4] A photographic diagram showing the result of western blotting of gp46 and actin (concentration 50 nM, examination of optimal culturing time).

All of the siRNAs inhibited the expression of gp46 protein remarkably compared with a vehicle (FIG. 2). In the experiment below, siRNA Sequence A, which showed the strongest effect, was used. Inhibition by siRNA was concentration dependent (FIG. 3); protein expression by gp46 was about 90% inhibited by 50 nM siRNA at 48 hours (FIG. 4).

Example 3

Inhibition of Collagen Synthesis by Prepared siRNA

Figure 5:
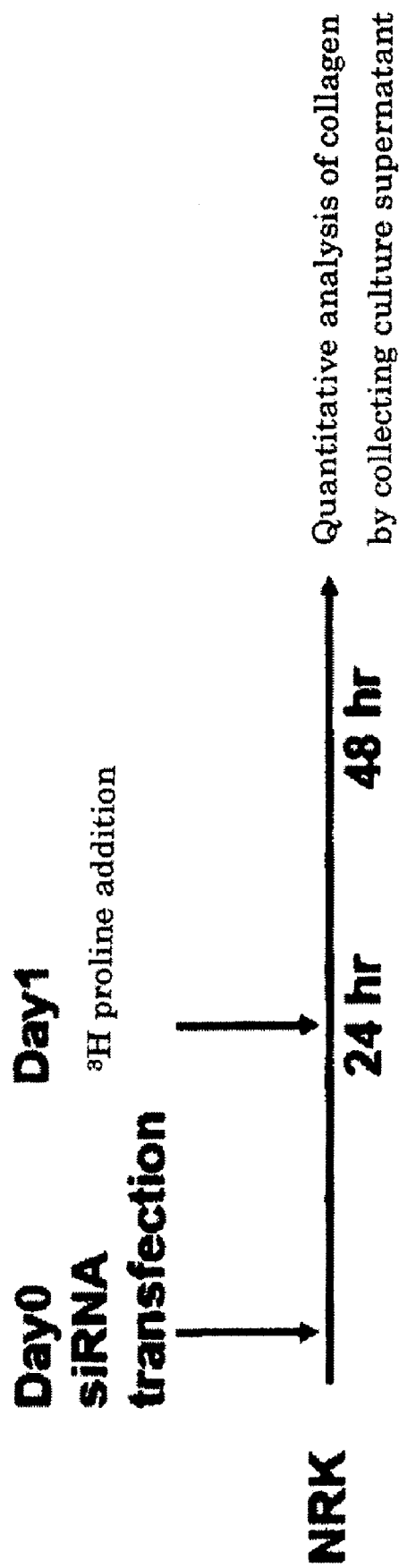
[FIG. 5] A diagram showing a protocol for evaluating inhibition of expression of collagen by gp46-siRNA in NRK cells.

In order to examine the amount of collagen synthesized, $^3$H-proline was added to the culture supernatant of rat fibroblasts (NRK cells) under the above-mentioned conditions (siRNA concentration 50 nM, time 48 hours), and after transfection the amount of $^3$H in secreted protein was examined (FIG. 5). The amount of collagen synthesized was calculated from the ratio of protein secreted in the supernatant to protein degraded by collagenase when culturing gp46siRNA-transfected fibroblasts in the presence of $^3$H-proline in accordance with a report by Peterkofsky et al. (Peterkofsky et al., Biochemistry. 1971 Mar 16; 10(6): 988-94).

$$\text{collagen synthesis ratio} = \frac{\text{collagenase-sensttive fraction} \times 100}{(5.4 \times \text{collagenase-insensitive fraction} + \text{collagenase-sensitive fraction})} \quad \text{[Equation 1]}$$

Figure 6:
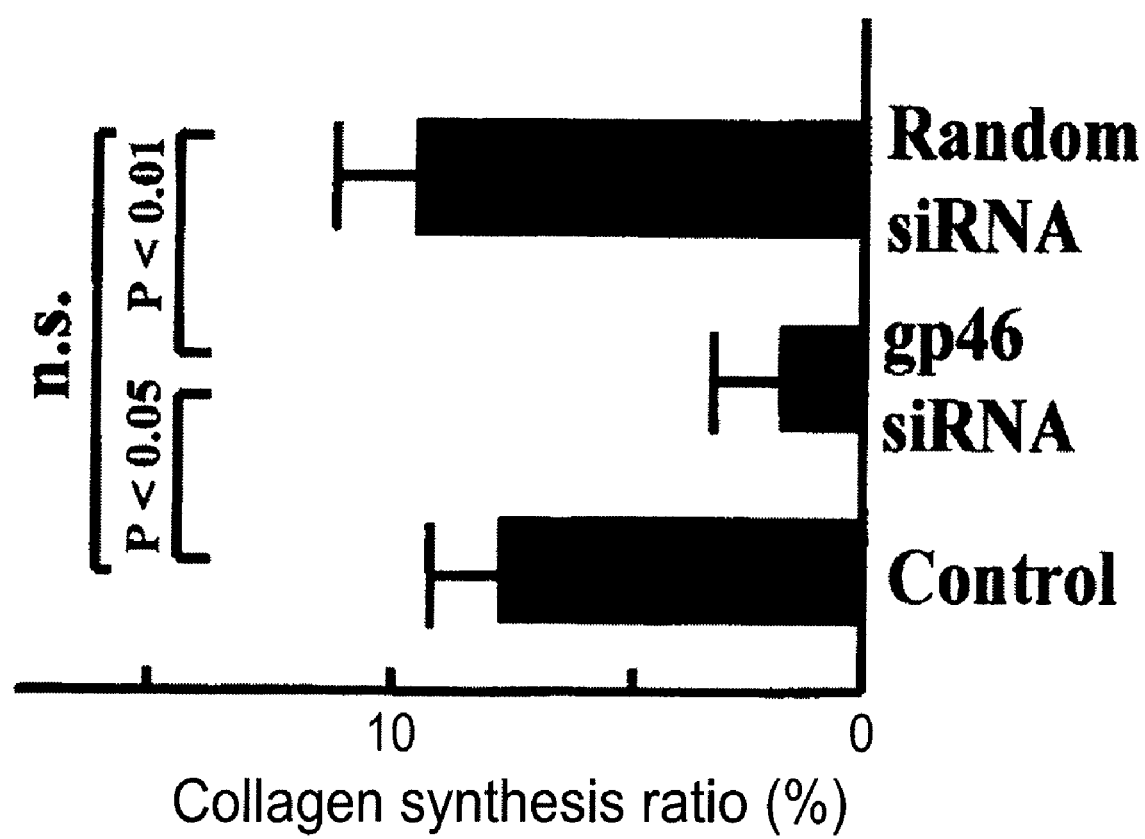
[FIG. 6] A graph showing inhibition of collagen synthesis by siRNA.

The collagen synthesis ratio in rat fibroblasts decreased by about 40% compared with a Control group (FIG. 6).

Example 4

Specific Transfection of Nucleic Acid into Hepatic Stellate Cells (HSC)

Figure 7:
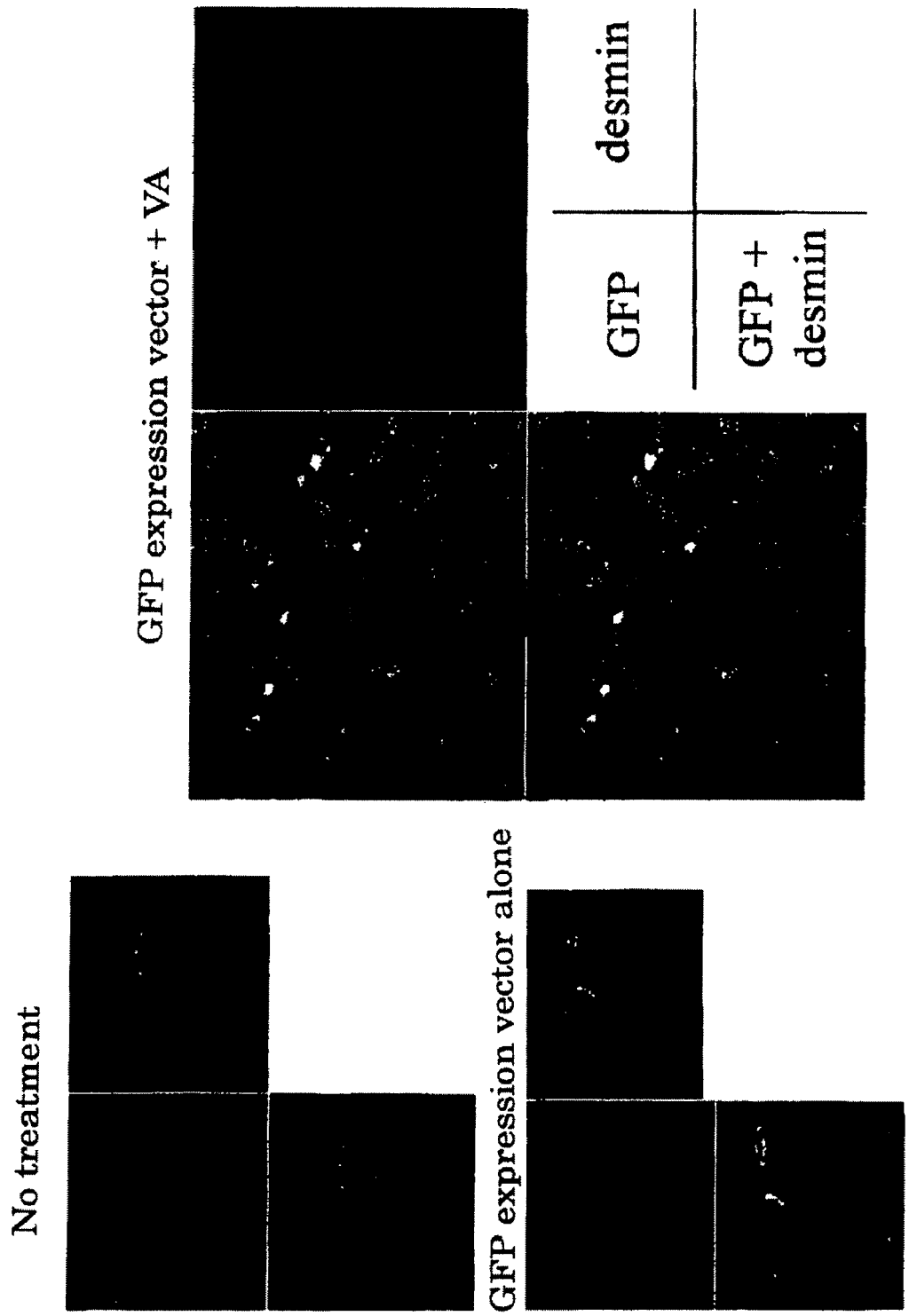
[FIG. 7] A photographic diagram showing HSC-specific siRNA transfection.

An emulsion (VA-Lip-GFP) was prepared by mixing GFP expression plasmid and liposome-encapsulated VA formed by mixing 10% VA and liposome, and after it was intraportally administered to a rat, hepatic tissue was collected and fixed. The emulsion was prepared by supposing that the amount of plasma for a 200 g rat was about 10 mL, and setting the concentrations of VA and GFP in portal blood at 10 μM. Specifically, 25 mg of all-trans-retinol (VA) was first dissolved in 87 μL of DMSO thus to give a 100 mM stock solution. 1 μL of this VA stock solution was mixed with 10 μL of lipofectamine and 179 μL of PBS, 10 μg of GFP expression plasmid was further added thereto to give a total of 200 and the mixture was vortexed for 3 minutes to give VA-Lip-GFP. The abdomen of an SD rat was opened, and the VA-Lip-GFP was slowly injected into a peripheral portal vein. 48 hours after the injection, hepatic tissue was harvested. Since compared with other hepatic cells intermediate filament desmin is specifically expressed in hepatic stellate cells (HSC), when fixed hepatic tissue was stained with Alexa Fluor 568-labeled anti-desmin antibody, and a fluorescence double image with GFP was examined, it was confirmed that GFP was expressed within the hepatic stellate cells (HSC) (FIG. 7). For untreated controls and a group to which the GFP expression plasmid vector alone was administered, expression in rat hepatic stellate cells was not observed, but in a group to which VA-Lip-GFP was administered, expression of GFP was observed specifically in stellate cells.

Example 5

Quantitative Analysis of Nucleic Acid Transfection Rate

Figure 8:
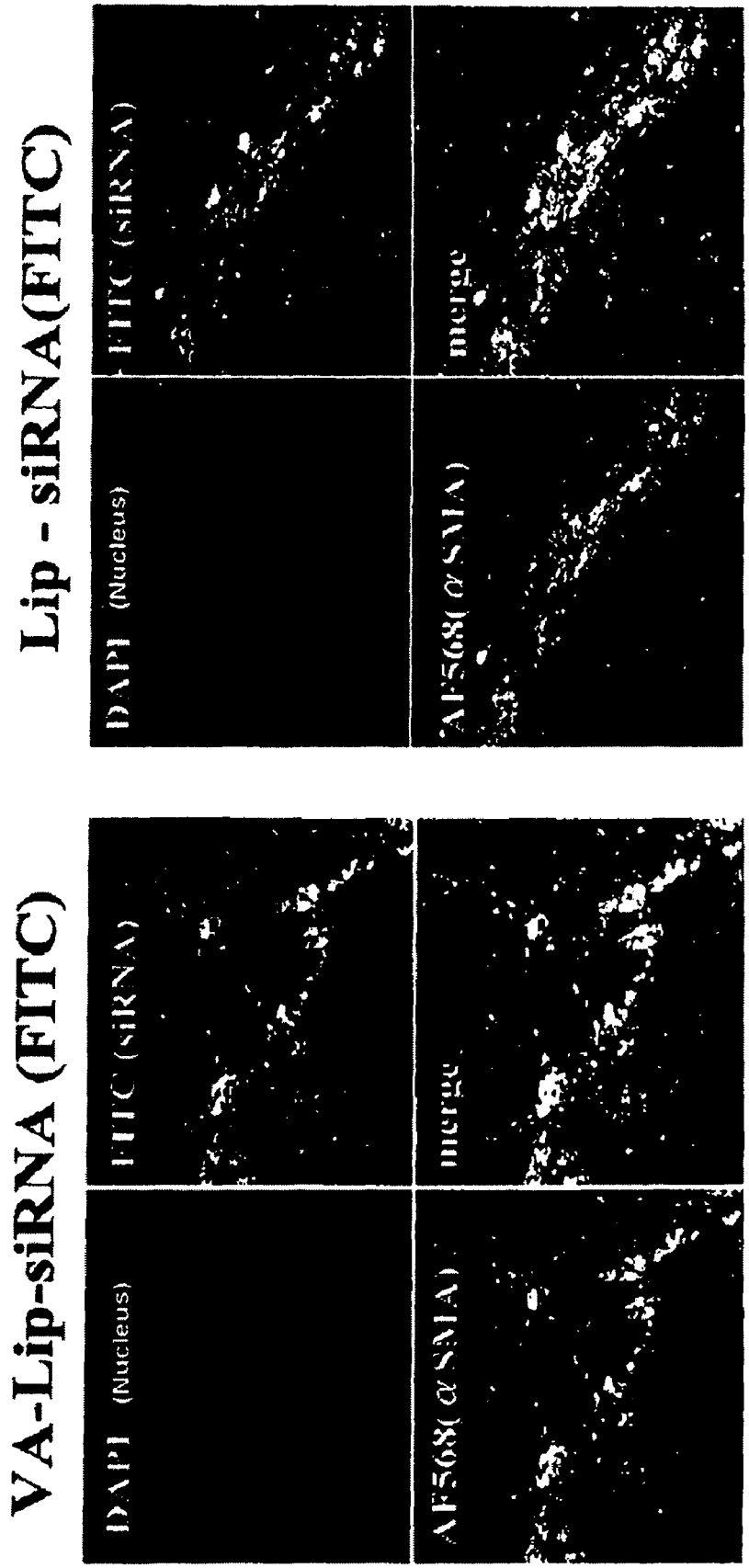
[FIG. 8] A photographic diagram for evaluating HSC-specific siRNA transfection percentage.

In the same manner as in Example 4, except that FITC-labeled gp46siRNA was used instead of the GFP expression plasmid, an emulsion (VA-Lip-gp46siRNA (FITC)) containing VA-encapsulated liposome and FITC-labeled gp46siRNA was prepared, and intraportally administered to an SD rat (10 μg as the amount of siRNA/200 μL). 48 hours after administration hepatic tissue was harvested, aSMA (smooth muscle actin), which compared with other hepatic cells is expressed specifically in HSC, was stained with Alexa Fluor 568-labeled anti-aSMA antibody, cell nuclei were stained with DAPI, and a fluorescence image was examined by a confocal laser scanning microscope (LSM). As shown on the left-hand side of FIG. 8, in a group to which VA-Lip-gp46siRNA (FITC) was administered, a large number of cells emitting both green fluorescence due to FITC and red fluorescence due to Alexa Fluor 568 were observed, and when a quantitative analysis was carried out by NIH Image (the number of cells was counted by selecting any 10 fields from a ×1000 fluorescence microscope photograph), the transfection efficiency was 77.6% (average of 10 fields). On the other hand, in a group to which Lip-gp46siRNA (FITC) containing no VA was administered, the transfection efficiency was a low value of 14.0% and, moreover, transfection into cells other than stellate cells was observed at 3.0% (right-hand side of FIG. 8). It has been found from the results above that the transfection efficiency into stellate cells is increased remarkably by including VA.

Example 6

Inhibition of Expression of gp46 by VA-Lip-gp46siRNA

Figure 9:
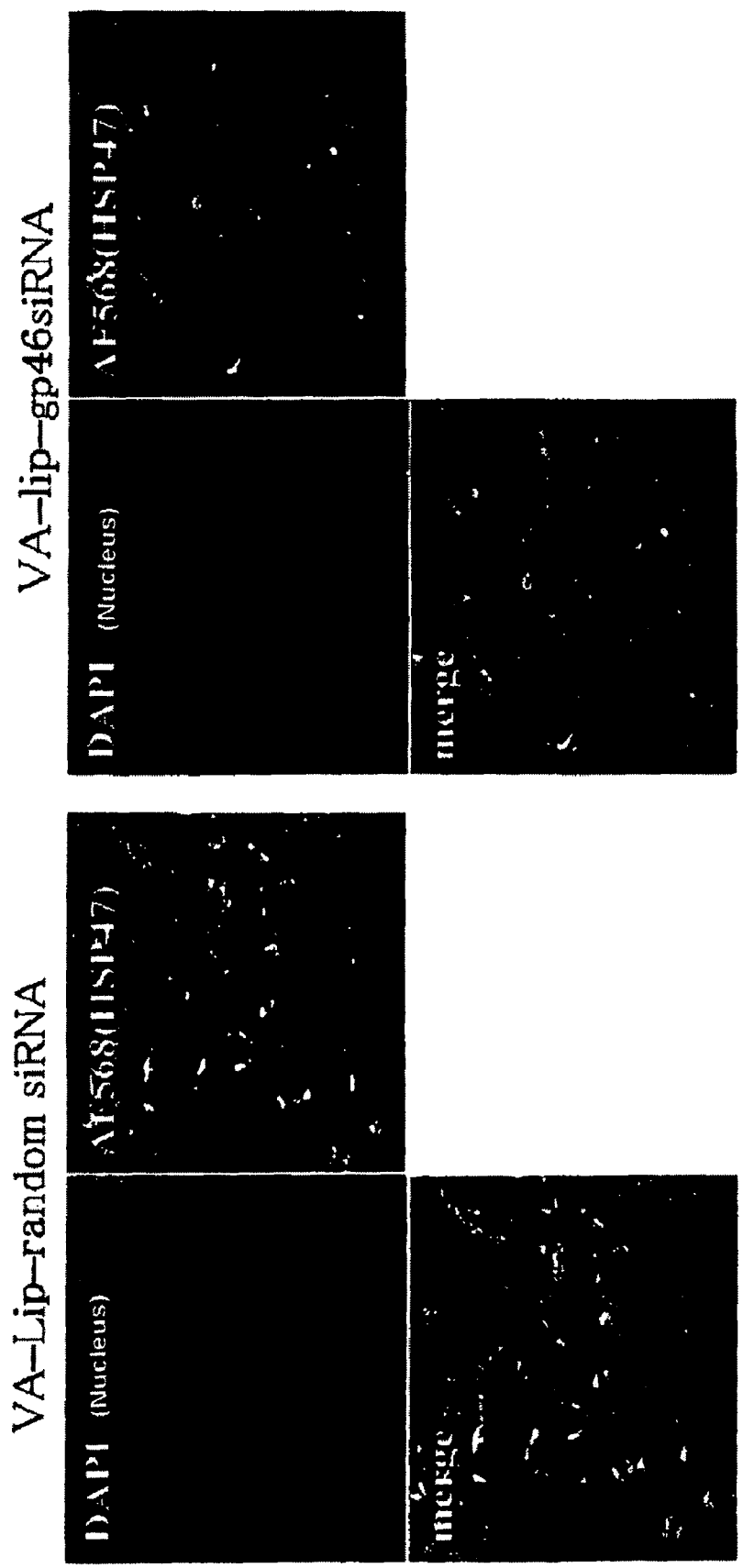
[FIG. 9] A photographic diagram for evaluating inhibition of expression of gp46 by siRNA.

With regard to another section of the tissue harvested in Example 5, gp46 was stained with Alexa Fluor 568-labeled anti-HSP47 antibody and cell nuclei were stained with DAPI, and a fluorescence image was examined by a confocal laser scanning microscope. As shown in FIG. 9, it was observed that in a group to which VA-Lip-gp46siRNA was administered, expression of gp46, which can be observed as a red fluorescence (right-hand side in the figure), was markedly reduced compared with a control group to which was administered VA-Lip-random siRNA containing random siRNA, which was not specific to gp46 (left-hand side in the figure). The expression inhibition rate relative to an average of 6 fields of the control group was 75%, which was extremely high, when the number of gp46-negative cells was examined by selecting any 10 fields from a ×1000 fluorescence microscope photograph using NIH Image in the same manner as in Example 7.

Example 7

Treatment of LC Rat (Intraportal Administration 1)

Figure 10:
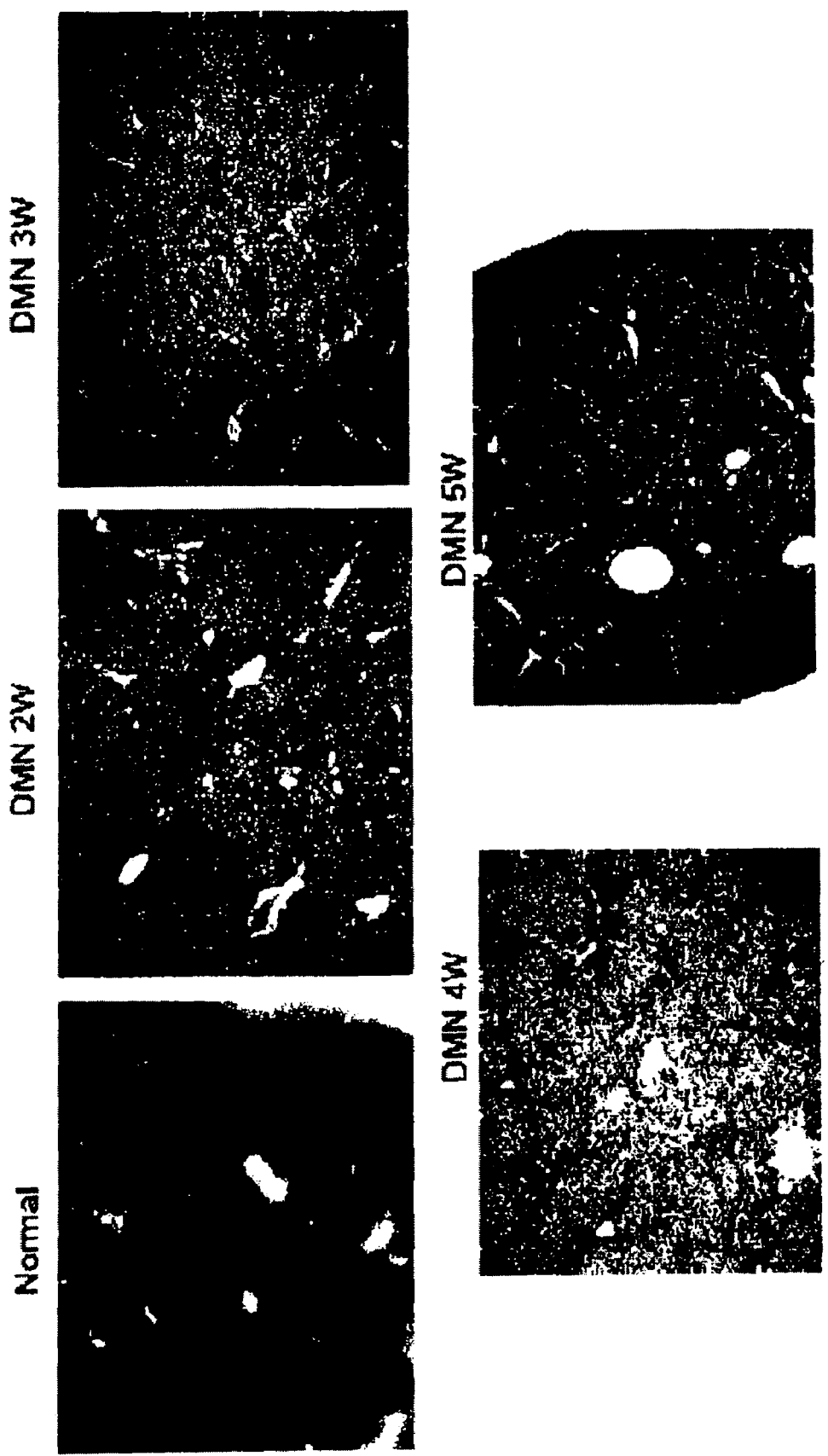
[FIG. 10] A photographic diagram showing azan staining of rat liver to which DMN had been administered.
Figure 11:
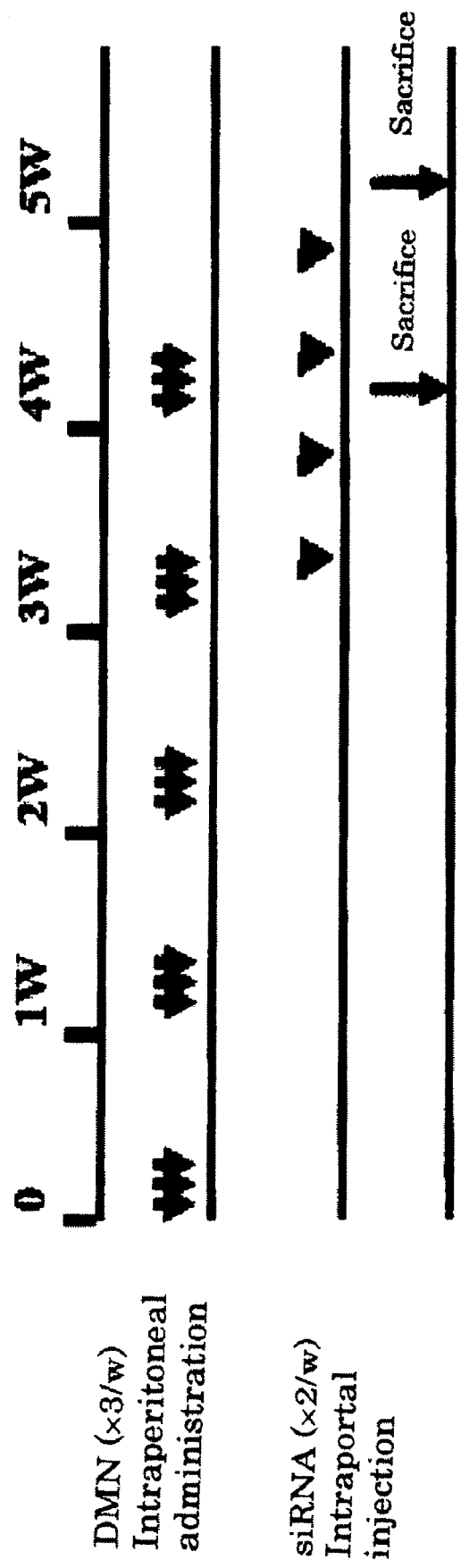
[FIG. 11] A diagram showing an LC rat treatment protocol.
Figure 12:
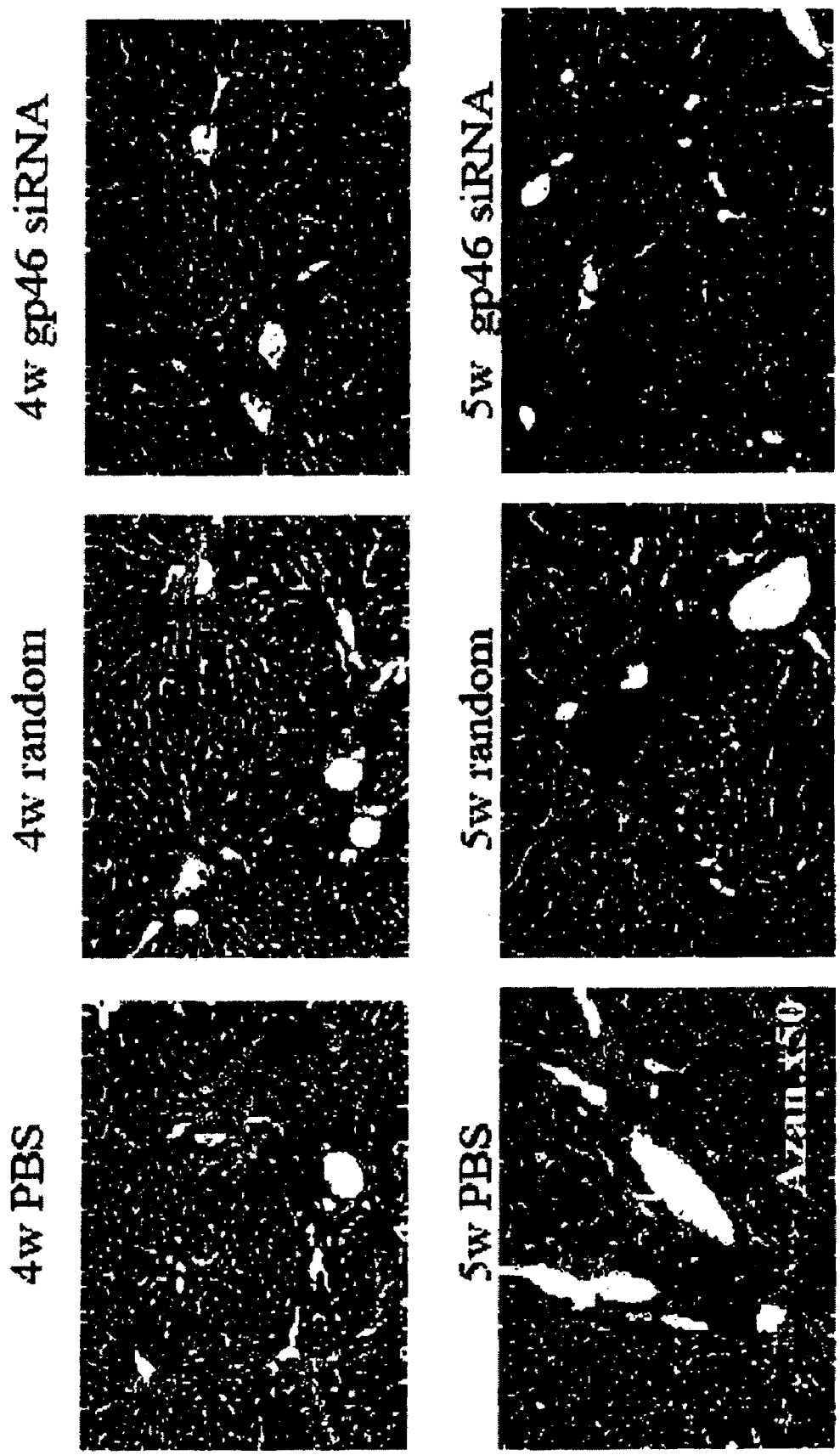
[FIG. 12] A photographic diagram showing azan staining of LC rat liver to which VA-Lip-gp46siRNA had been administered.
Figure 13:
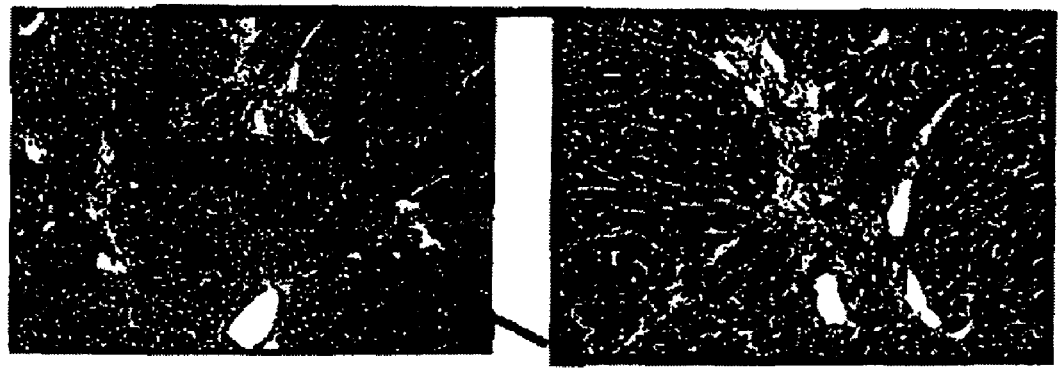
[FIG. 13] A diagram showing a method for extracting a stained portion by means of NIH Image (6 positions being randomly taken from an azan-stained image).
Figure 13:
Figure 13:
Figure 14:
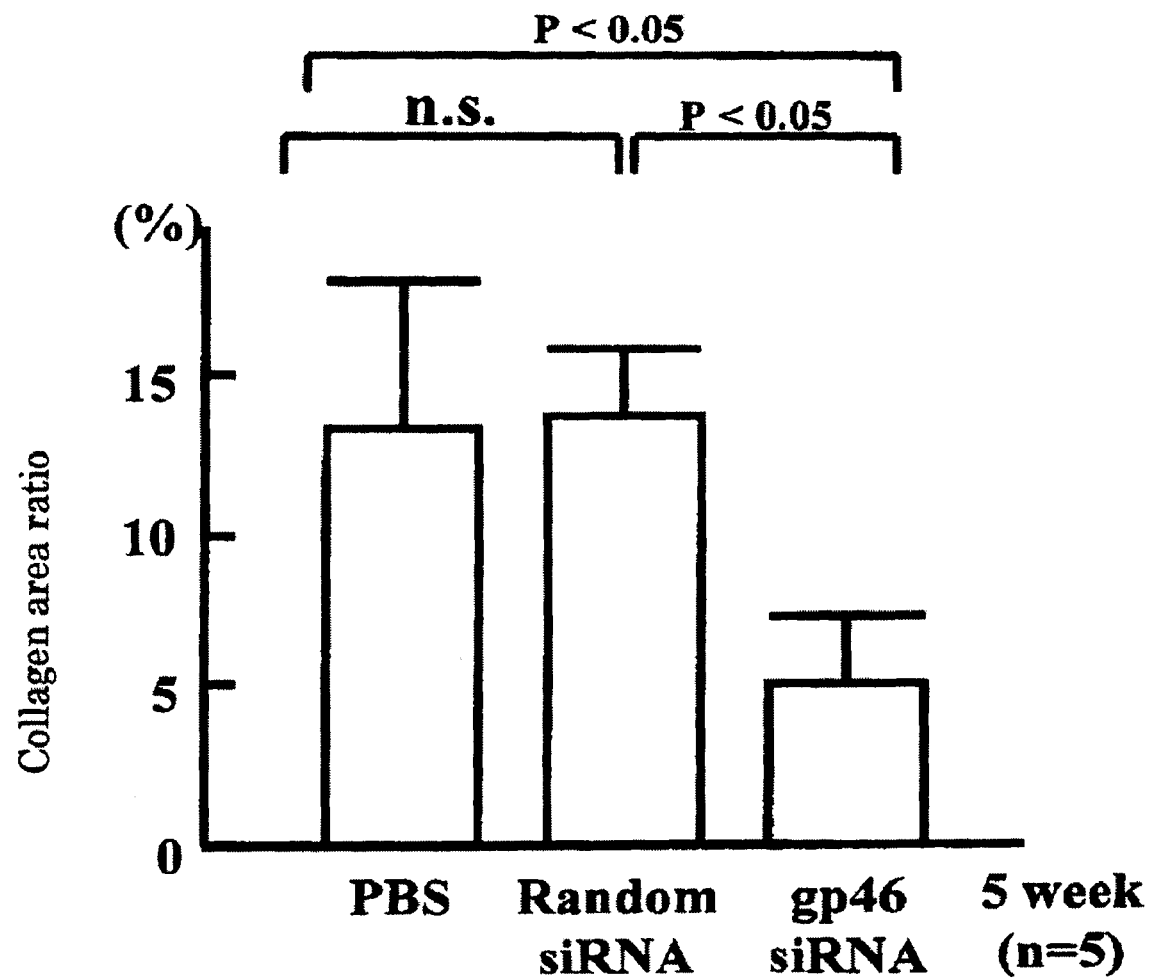
[FIG. 14] A graph showing the ratio by area occupied by fibrotic portions in liver histology (Collagen ratio by area, %).
Figure 15:
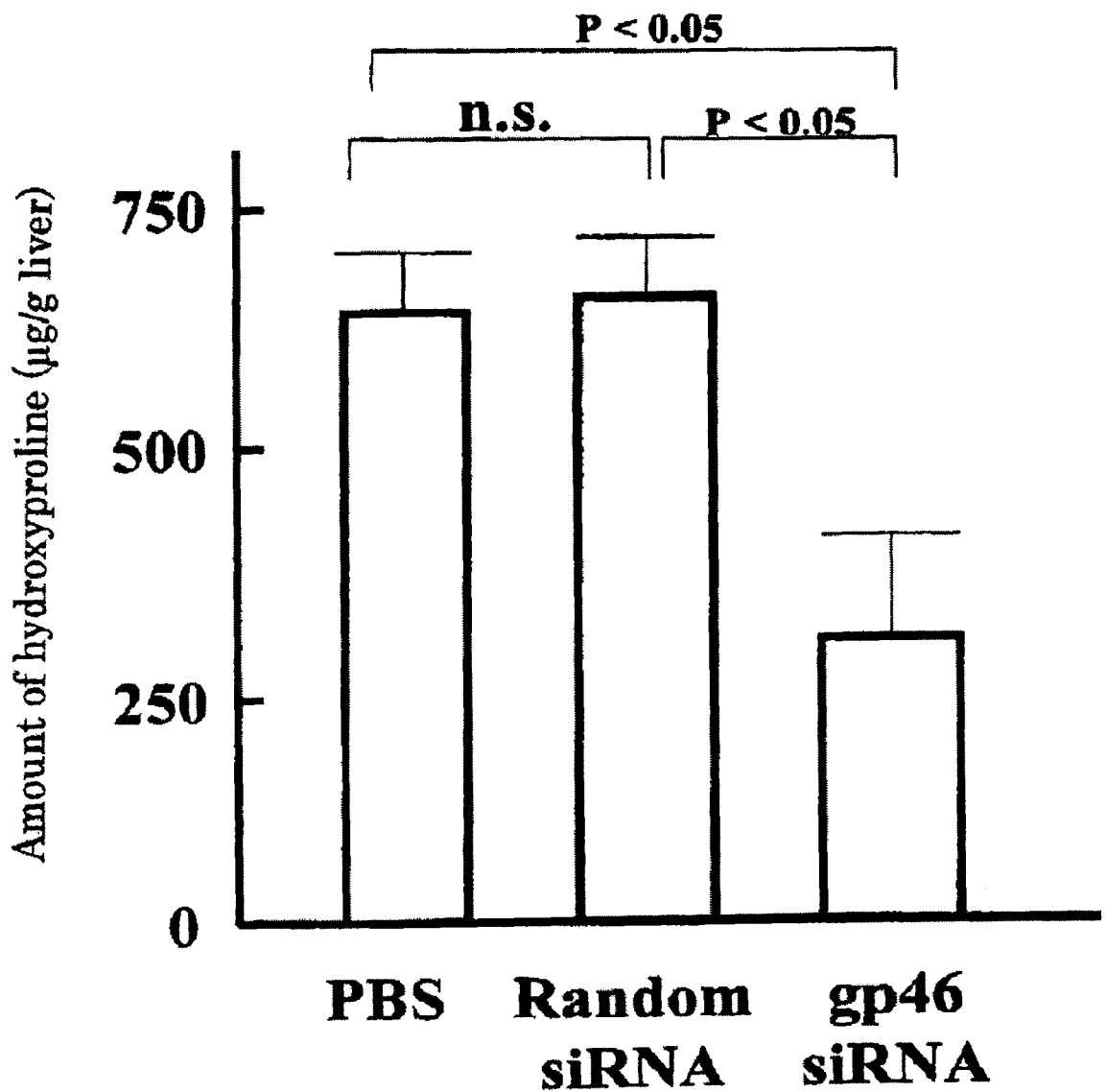
[FIG. 15] A graph showing the amount of hydroxyproline in hepatic tissue.

In accordance with a report by Jezequel et al. (Jezequel A M et al., J Hepatol. 1987 October; 5(2): 174-81), an LC model rat was prepared using Dimethylnitrosamine (DMN) (FIG. 10). Specifically, a 1 mL/kg dose of 1% Dimethylnitrosamine (DMN) (intraperitoneal administration) was administered to a 5 week-old SD rat (male) 3 straight days per week. As already reported, an increase in fiber was observed from the 2nd week, and in the 4th week this was accompanied by the findings of marked fibrosis, destruction of hepatic lobule structure, and formation of regenerative nodules being observed (FIG. 11). Then, by the same method as in Example 4, an emulsion (VA-Lip-gp46siRNA) was prepared by formulating gp46siRNA as a liposome and mixing with 10% VA, and was administered. Administration of VA-Lip-gp46siRNA was started in the 3rd week, by which time sufficient fibrosis was observed, and evaluation was carried out in the 4th and 5th weeks. Since it was confirmed by Example 2 that the effects were observed for up to 48 hours in vitro, administration was carried out twice a week (FIG. 11). The amount administered was determined in accordance with a report in which siRNA was directly injected (McCaffery et al., Nature. 2002 Jul. 4; 418(6893): 38-9), and was 40 μg as the total amount of siRNA. From azan staining of the liver after administration of siRNA, in the 4th week there was no apparent difference between a group to which saline had been administered, a group to which siRNA (random) had been administered, and a group to which siRNA (gp46) had been administered, but in the 5th week a decrease in the amount of fiber was observed for the group to which gp46siRNA had been administered (FIG. 12). In order to quantitatively analyze the amount of fiber, an unstained portion was extracted using NIH Image, its area was measured (FIG. 13), and a significant decrease in the area of collagen was observed for the group to which gp46siRNA had been administered (FIG. 14). Furthermore, in order to evaluate the degree of fibrosis using another measure, the amount of hydroxyproline, which is an indicator for fibrosis, was quantitatively measured by a standard method. Specifically, after 20 mg of freeze-dried hepatic tissue was hydrolyzed with HCl for 24 hours, the reaction liquid was centrifuged, and the supernatant was treated with a reagent such as Ehrlich's solution and centrifuged. The supernatant was recovered, and the amount of hydroxyproline in the hepatic tissue was measured by measuring the absorbance at 560 nm (Hepatology 1998 November; vol. 28: 1247-1252). As shown in FIG. 15, in the group to which gp46siRNA had been administered, the amount of hydroxyproline became very small.

Example 8

Treatment of LC Rat (Intraportal Administration 2)

Figure 16:
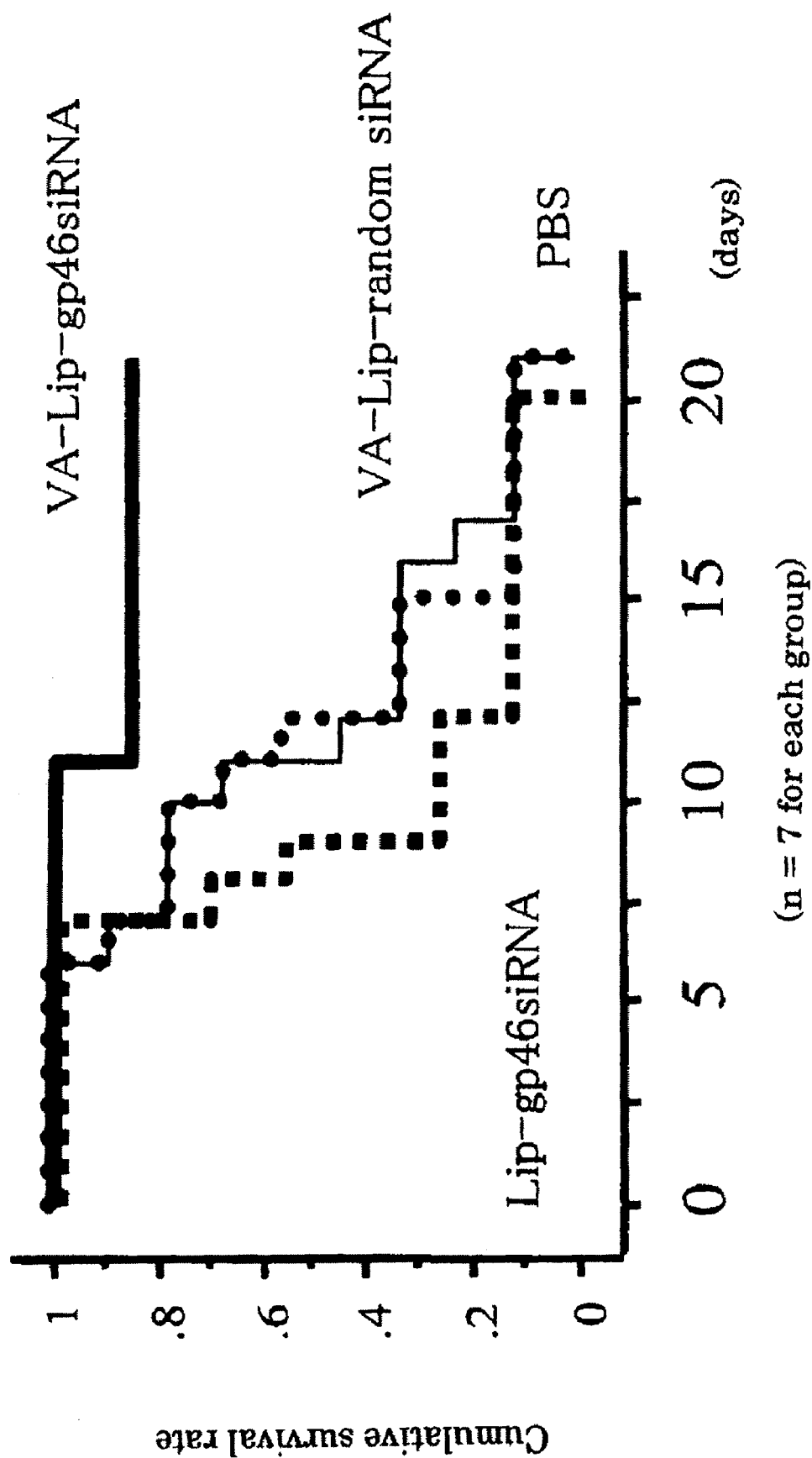
[FIG. 16] A graph showing a survival curve for hepatic cirrhosis rat to which VA-Lip-gp46siRNA had been intraportally administered.
Figure 17:
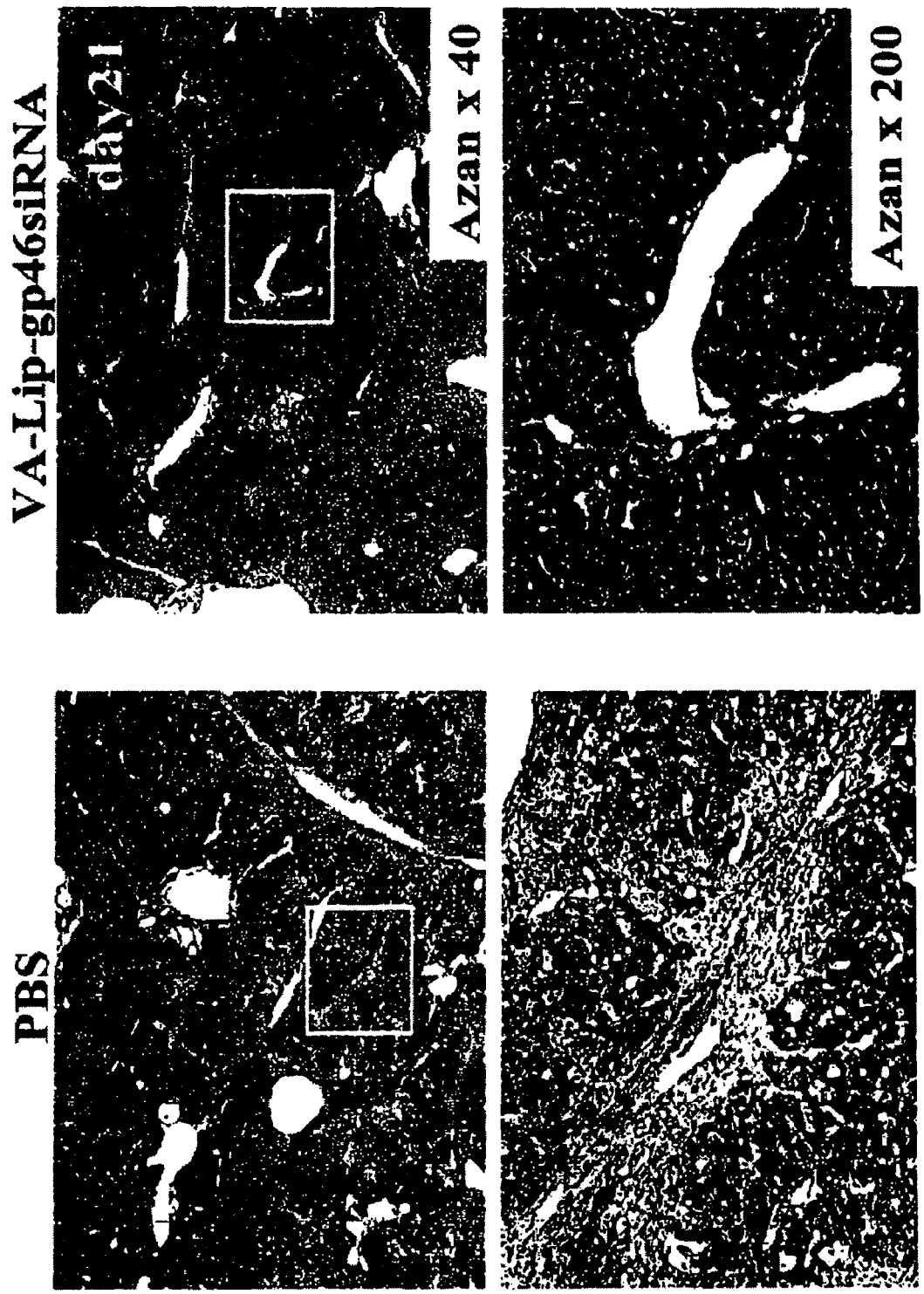
[FIG. 17] A photographic diagram showing azan staining of hepatic tissue of hepatic cirrhosis rat to which VA-Lip-gp46siRNA had been intraportally administered.

Furthermore, in order to examine a change in the survival rate by administration of the medicine of the present invention, in accordance with a method by Qi Z et al. (Proc Natl Acad Sci USA. 1999 Mar. 2; 96(5): 2345-9.), an LC model rat was prepared using Dimethylnitrosamine (DMN) in an amount that was increased by 20% over the normal amount. In this model, a total of 4 intraportal administrations were carried out in the 1st and 2nd weeks. Administration details were: PBS, Lip-gp46siRNA, VA-Lip-random siRNA, and VA-Lip-gp46siRNA (n=7 for each group). After the 3rd week, all of the controls (the group to which PBS had been administered, the group to which VA-Lip-random siRNA had been administered, and the group to which Lip-gp46siRNA had been administered) were dead, but 6 out of 7 survived for the group to which VA-Lip-gp46siRNA had been administered (FIG. 16). Furthermore, in azan staining of the liver on the 21st day, an apparent decrease in the amount of fiber was observed for the group to which gp46siRNA had been administered (FIG. 17).

Example 9

Treatment of LC Rat (Intraportal Administration 3)

In another experiment, intraportal administration was carried out from the 3rd week for LC model rats (1% DMN 1 mg/kg intraperitoneally administered 3 times a week) prepared in accordance with the method by Qi Z et al. and a method by Ueki T et al. (Nat Med. 1999 February; 5(2): 226-30), as shown in the table below (n=6 for each group). PBS was added to each substance to be administered so as to make a total volume of 200 μL, and the frequency of administration was once a week.

TABLE 1

| Treatment group | Content of administration | Dosage |
| --- | --- | --- |
| 9-1 | VA | VA 200 nmol |
| 9-2 | Lip-gp46siRNA | liposome 100 nmol, gp46siRNA 20 μg |
| 9-3 | VA-Lip-random siRNA | VA 200 nmol, liposome 100 nmol, random-siRNA 20 μg |
| 9-4 | VA-Lip-gp46siRNA | VA 200 nmol, liposome 100 nmol, gp46siRNA 20 μg |

Figure 18:
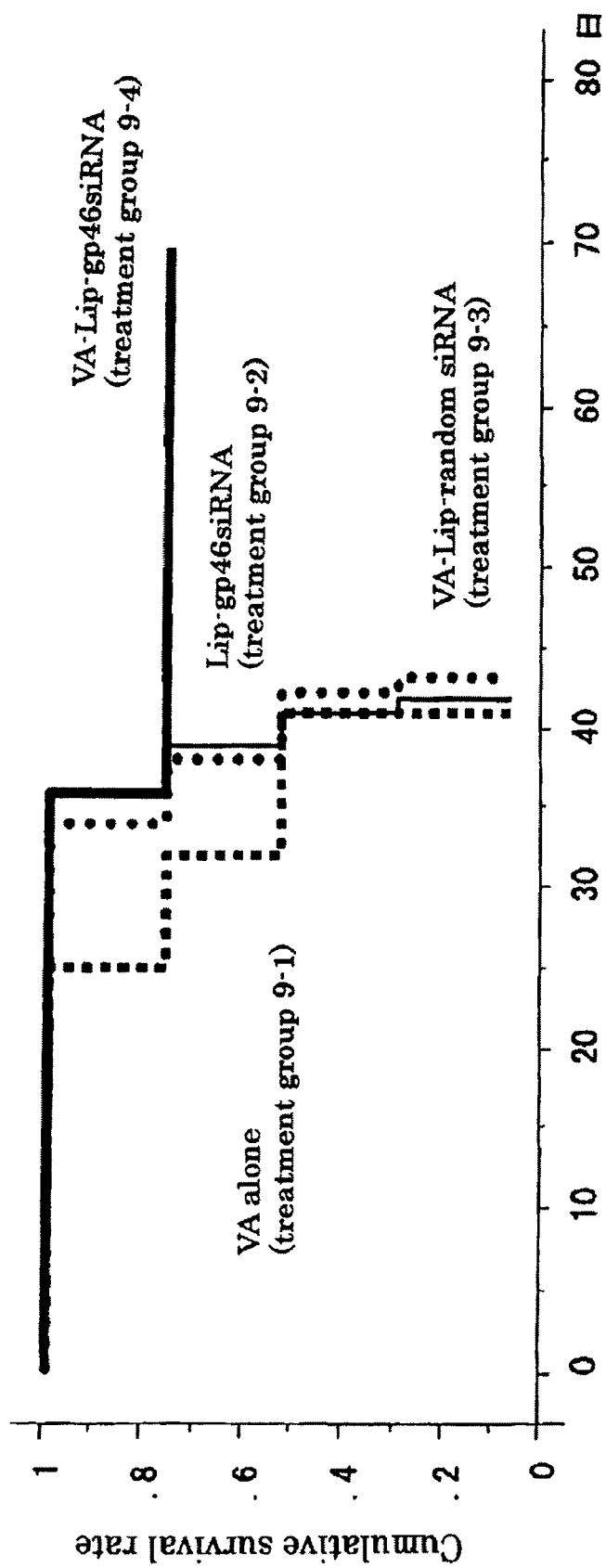
[FIG. 18] A graph showing a survival curve for hepatic cirrhosis rat to which VA-Lip-gp46siRNA had been intraportally administered.
Figure 19:
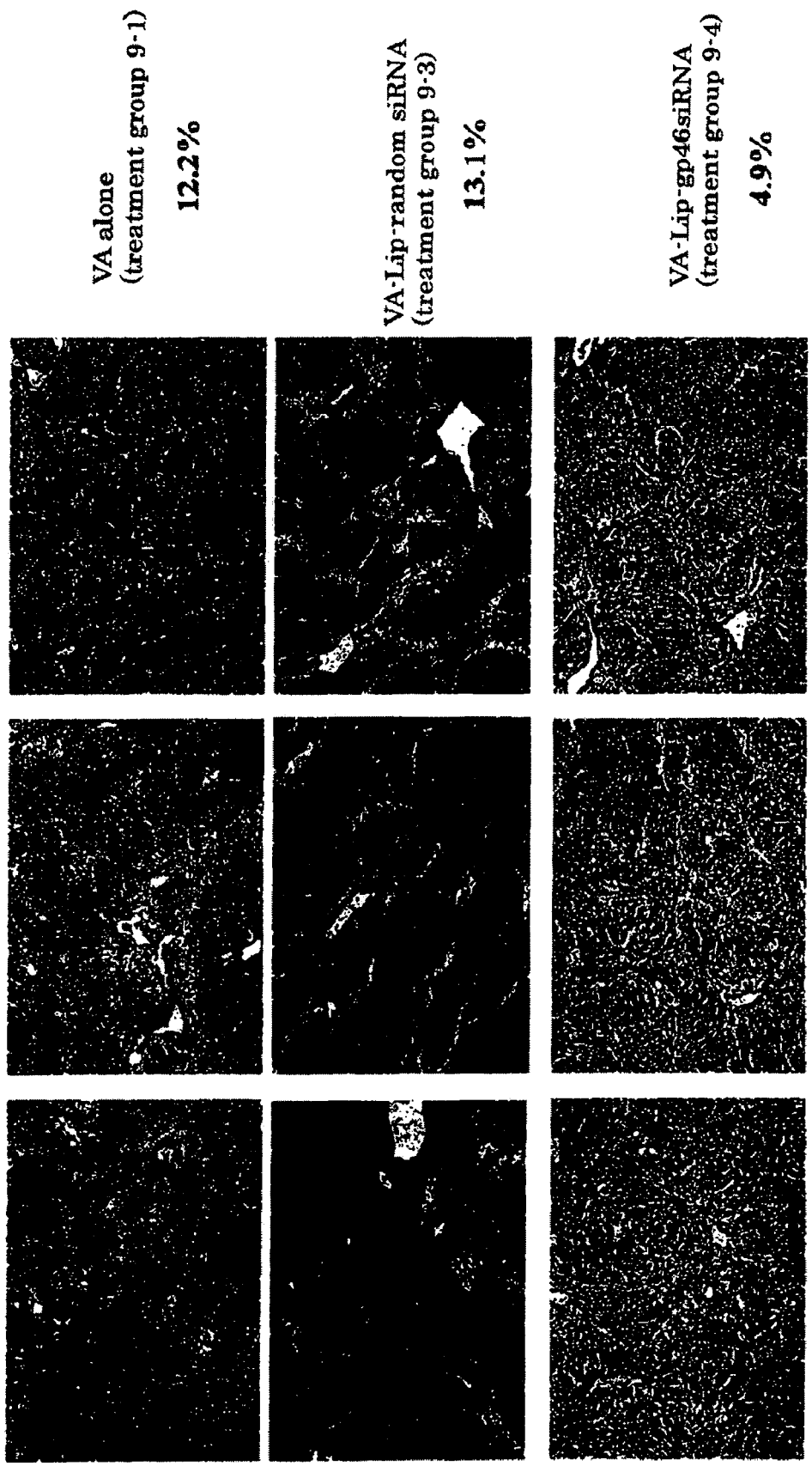
[FIG. 19] A photographic diagram showing azan staining of hepatic tissue of hepatic cirrhosis rat to which VA-Lip-gp46siRNA had been intraportally administered.

From the results, in the groups other than the group to which the medicine of the present invention had been administered (treatment group 9-4), all 6 rats were dead by the 45th day after starting administration of DMN, but in the group to which the medicine of the present invention had been administered, all of the individuals apart from one case, which was dead on the 36th day, survived for more than 70 days after starting administration of DMN (FIG. 18). For the dead individuals, the amount of hepatic fiber was quantitatively analyzed based on the area of collagen in the same manner as in Example 7, and the increase in the amount of hepatic fiber was remarkably inhibited by administration of VA-Lip-gp46siRNA (FIG. 19).

Example 10

Treatment of LC Rat (Intravenous Administration)

Intravenous administration was carried out from the 3rd week for LC model rats (1% DMN 1 μg/BW (g) intraperitoneally administered 3 times a week) prepared in the same manner as in Example 9, as shown in the table below (n=6 for each group). PBS was added to each substance to be administered so as to make a total volume of 200 μL. The administration period was up to death except that it was up to the 7th week for Group 10-4 and the 6th week for Group 10-10.

TABLE 2

| Treatment group | Content of administration | Dosage | Frequency of administration |
| --- | --- | --- | --- |
| 10-1 | VA | VA 200 nmol | Twice a week |
| 10-2 | Lip-gp46siRNA | liposome 100 nmol, gp46siRNA 100 μg | |
| 10-3 | VA-Lip-random siRNA | VA 200 nmol, liposome 100 nmol, random-siRNA 100 μg | |
| 10-4 | VA-Lip-gp46siRNA | VA 200 nmol, liposome 100 nmol, gp46siRNA 100 μg | |
| 10-5 | PBS | 200 μL | Three times a week |
| 10-6 | VA | VA 200 nmol | |
| 10-7 | VA-Lip | VA 200 nmol, liposome 100 nmol | |
| 10-8 | Lip-gp46siRNA | liposome 100 nmol, gp46siRNA 150 μg | |
| 10-9 | VA-Lip-random siRNA | VA 200 nmol, liposome 100 nmol, random-siRNA 150 μg | |
| 10-10 | VA-Lip-gp46siRNA | VA 200 nmol, liposome 100 nmol, gp46siRNA 150 μg | |

Figure 20:
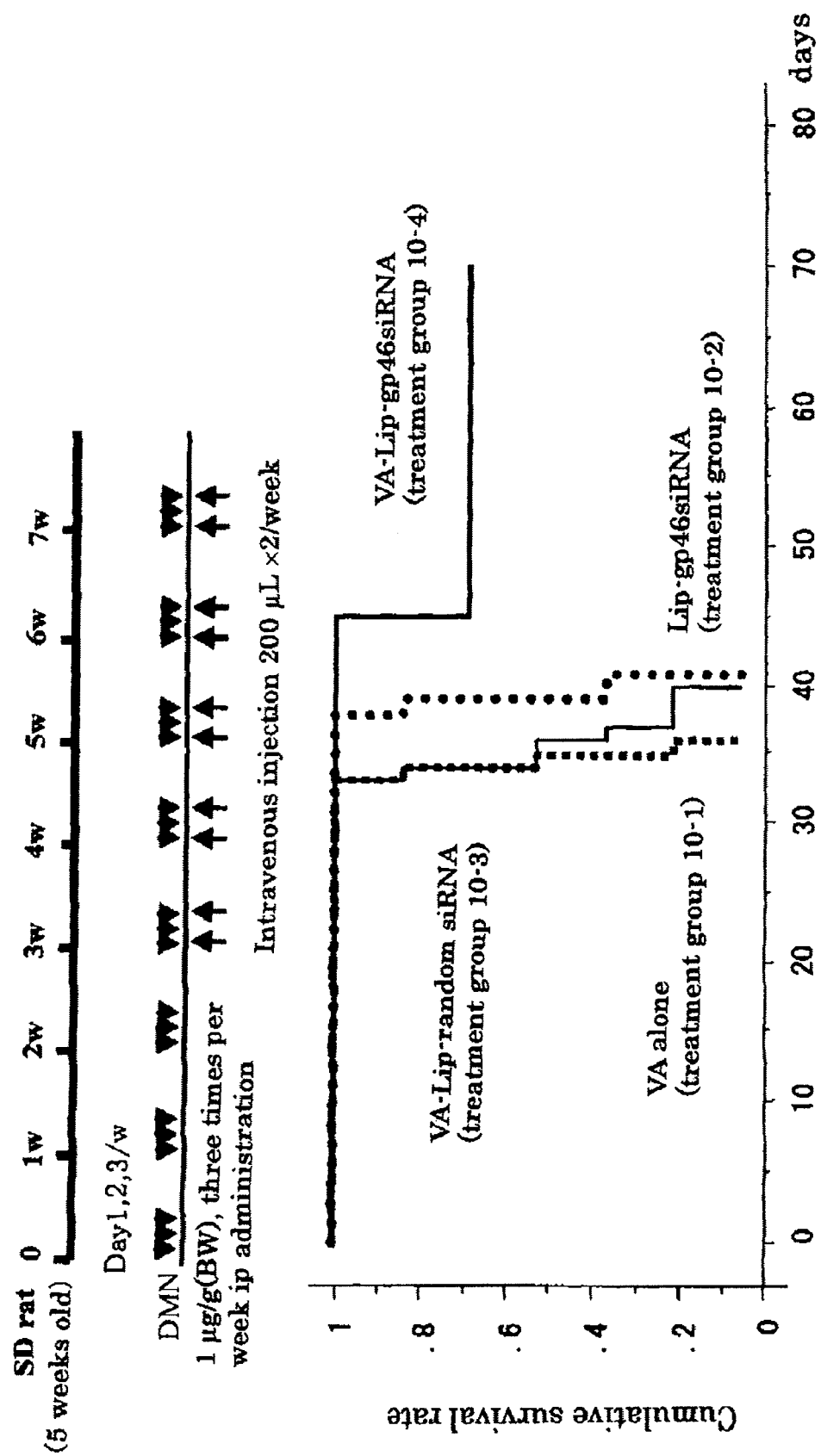
[FIG. 20] A graph showing a survival curve for hepatic cirrhosis rat to which VA-Lip-gp46siRNA had been intravenously administered.
Figure 21:
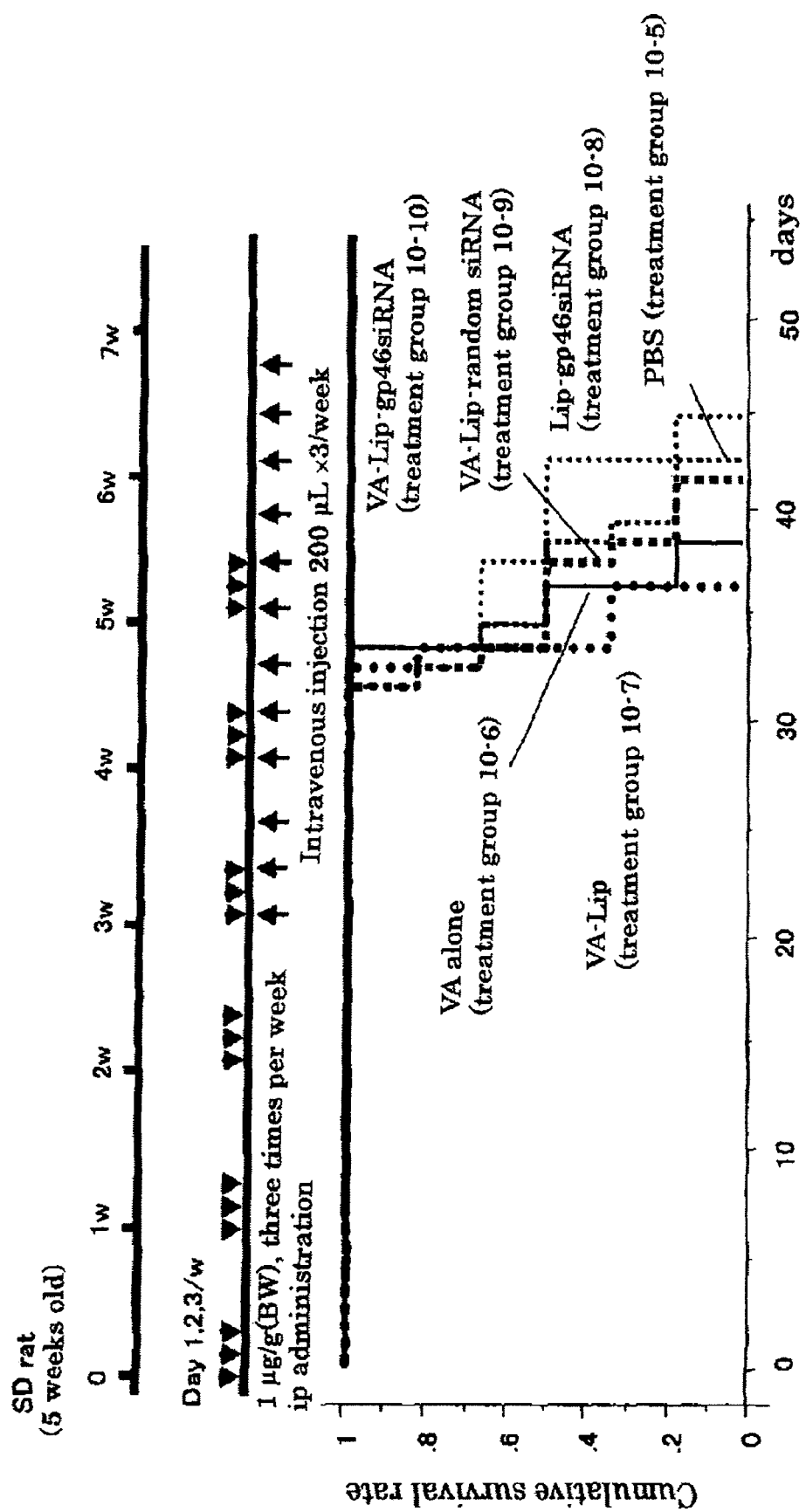
[FIG. 21] A graph showing a survival curve for hepatic cirrhosis rat to which VA-Lip-gp46siRNA had been intravenously administered.
Figure 22:
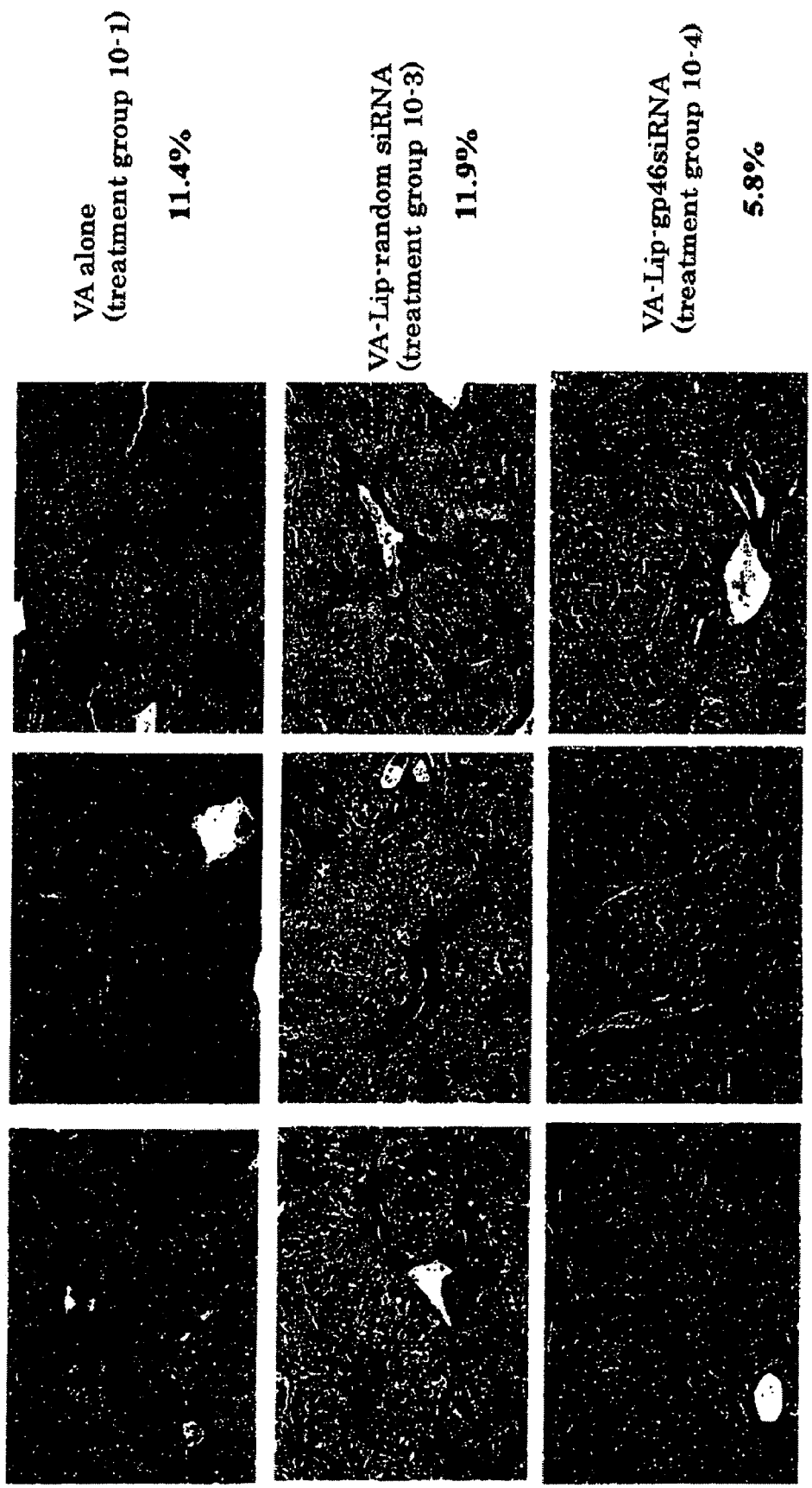
[FIG. 22] A photographic diagram showing azan staining of hepatic tissue of hepatic cirrhosis rat to which VA-Lip-gp46siRNA had been intravenously administered.

From the results, in the groups other than the groups to which the medicine of the present invention had been administered (treatment groups 10-4 and 10-10), all 6 rats were dead by the 45th day after starting administration of DMN, but in the groups to which the medicine of the present invention had been administered, all of the individuals, apart from a case in which two rats were dead on the 45th day in treatment group 10-4, survived for more than 70 days after starting administration of DMN (FIGS. 20 and 21). For the dead individuals, the amount of hepatic fiber was quantitatively analyzed in the same manner as in Example 7, and the increase in the amount of hepatic fiber was remarkably inhibited by administration of VA-Lip-gp46siRNA (FIG. 22).

The above-mentioned results show that the medicine of the present invention is extremely effective for the prevention and treatment of fibrosis, in which stellate cells are involved.

Example 11

Improvement of Results by RBP (Retinol-Binding Protein)

Figure 23:
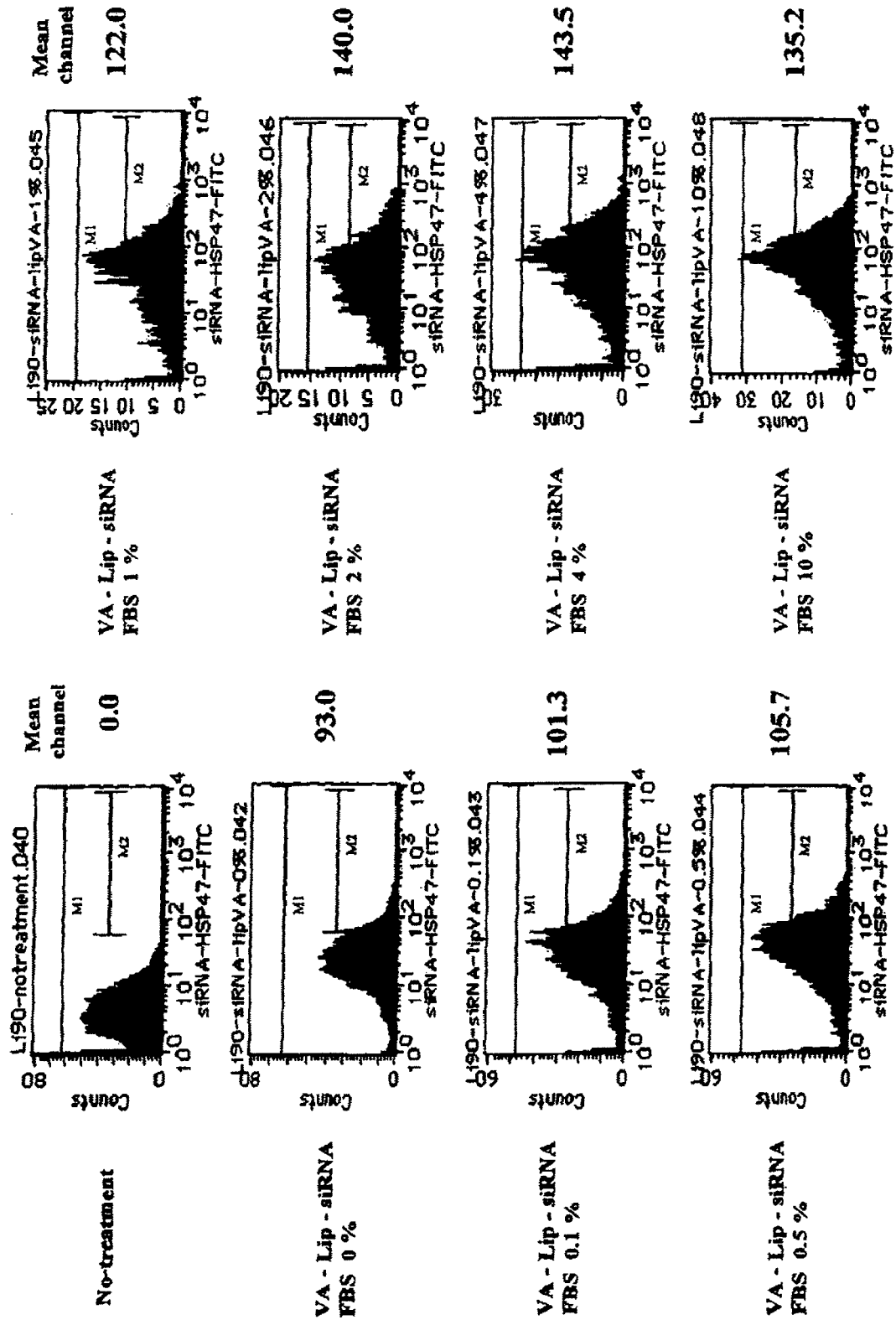
[FIG. 23] A diagram showing improvement of VA-Lip-gp46siRNA transfection efficiency by RBP.
Figure 24:
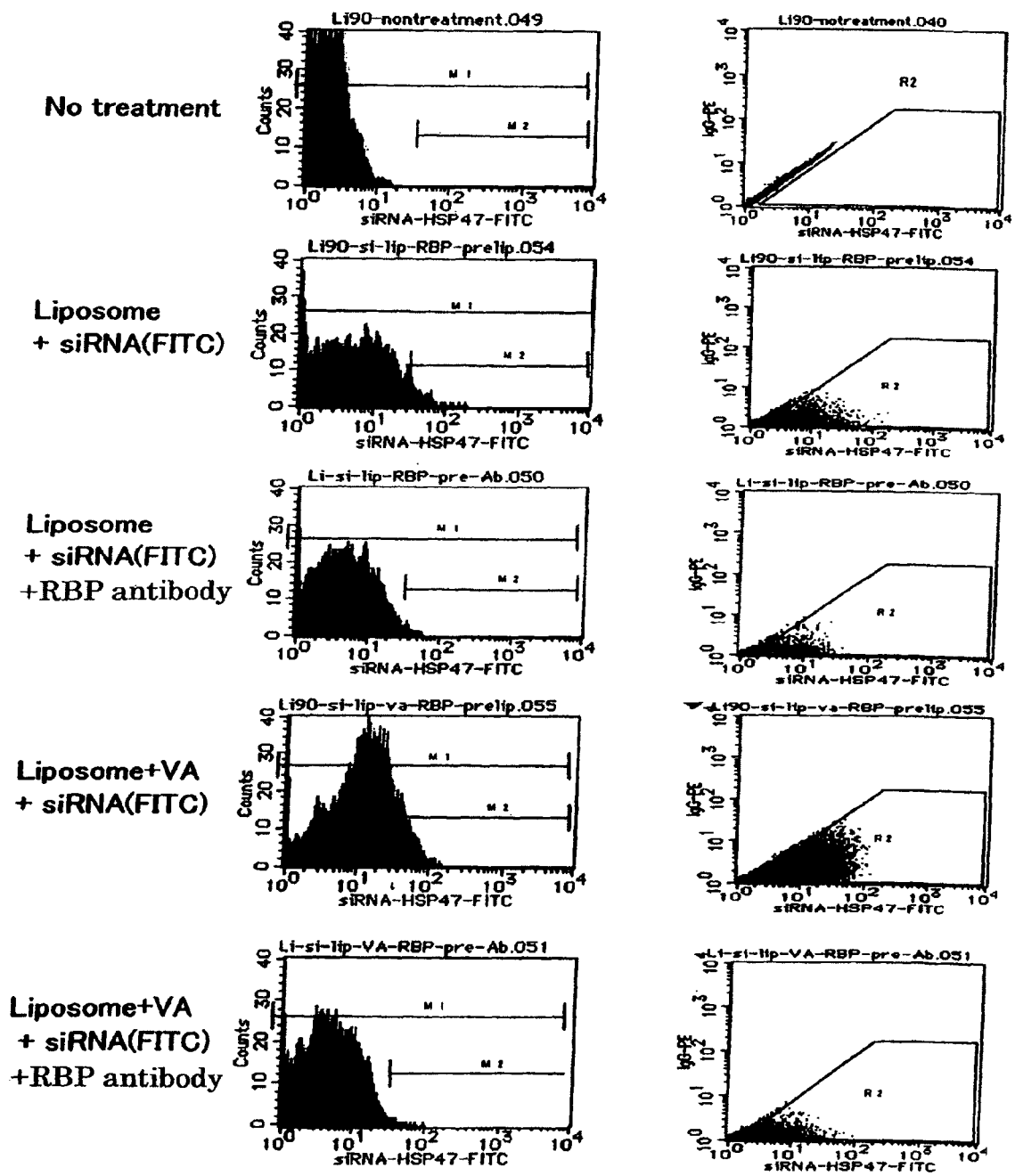
[FIG. 24] A diagram showing inhibition of VA-Lip-gp46siRNA transfection by anti-RBP antibody.

The influence of RBP on VA-Lip-gp46siRNA transfection efficiency was examined using LI90, which is a cell line derived from human hepatic stellate cells. 100 nM of VA-Lip-gp46siRNA (FITC) prepared in Example 5, together with various concentrations (i.e. 0, 0.1, 0.5, 1, 2, 4, or 10%) of FBS (fetal bovine serum), were added to LI90 during culturing and incubated for 48 hours, a fluorescence image was observed by LSM, and the amount of siRNA incorporated into individual cells was quantitatively analyzed by FACS. FBS contained about 0.7 mg/dL of RBP. As shown in FIG. 23, FBS (RBP) gave a concentration-dependent increase in the amount of siRNA transfection. Subsequently, 100 nM of VA-Lip-gp46siRNA (FITC) and 4% FBS, together with 10 μg (21.476 nmol) of anti-RBP antibody, were added to LI90 during culturing, and the siRNA transfection efficiency was evaluated in the same manner. As shown in FIG. 24, the increase in the amount of transfection by RBP was markedly decreased by the addition of anti-RBP antibody. The above-mentioned results show that RBP is effective in further enhancing transfection of the medicine of the present invention.

What is claimed is:

1. A method of treating a stellate cell-related disorder, the method comprising administering an effective amount of a stellate cell-specific preparation to a subject in need thereof, wherein the stellate cell-specific preparation comprises: (i) a stellate cell-specific drug carrier comprising a stellate cell-specific amount of a retinoid and a drug carrier component other than the retinoid, and (ii) a drug in an amount effective for controlling the activity or growth of stellate cells.

2. The method of claim 1, wherein the drug for controlling the activity or growth of stellate cells is selected from the group consisting of a TGF β activity inhibitor, a preparation having HGF activity, an MMP production promoter, a TIMP production inhibitor, a PPARγ ligand, an angiotensin activity inhibitor, a PDGF activity inhibitor, a sodium channel inhibitor, an apoptosis inducer and a growth inhibitor.

3. The method of claim 1, wherein the drug for controlling the activity or growth of stellate cells is selected from the group consisting of an siRNA, ribozyme, antisense nucleic acid and DNA/RNA chimera polynucleotide; or a vector expressing same.

4. The method of claim 3, wherein the drug for controlling the activity or growth of stellate cells targets HSP47.

5. The method of claim 1, wherein the stellate cell-related disorder is selected from the group consisting of fibrosis, hepatitis and pancreatitis.

6. The method of claim 5, wherein the fibrosis is selected from the group consisting of hepatic fibrosis, hepatic cirrhosis, pancreatic fibrosis, vocal cord scarring, vocal cord mucosal fibrosis, and laryngeal fibrosis.

7. The method of claim 1, wherein the preparation is parenterally administered.

8. The method of claim 1, wherein the stellate cell-specific carrier is selected from the group consisting of a polymer micelle, liposome, emulsion, microsphere, and nanosphere.

9. A method of treating a fibrotic disorder, comprising administering an effective amount of a stellate cell-specific preparation to a subject in need thereof, wherein the stellate cell-specific preparation comprises: (i) a stellate cell-specific drug carrier comprising a stellate cell-specific amount of a retinoid and a drug carrier component other than the retinoid, and (ii) a drug in an amount effective for controlling the activity or growth of stellate cells.

10. The method of claim 9, wherein the fibrotic disorder is fibrosis.

11. The method of claim 10, wherein the fibrosis is selected from the group consisting of hepatic fibrosis, hepatic cirrhosis, pancreatic fibrosis, vocal cord scarring, vocal cord mucosal fibrosis, and laryngeal fibrosis.

12. The method of claim 9, wherein the fibrotic disorder is hepatic fibrosis, the stellate cell-specific carrier is a liposome, the retinoid is vitamin A, and the drug is an siRNA that targets HSP47.

13. The method of claim 9, wherein the fibrotic disorder is hepatic cirrhosis, the stellate cell-specific carrier is a liposome, the retinoid is vitamin A, and the drug is an siRNA that targets HSP47.

14. The method of claim 9, wherein the fibrotic disorder is pancreatic fibrosis, the stellate cell-specific carrier is a liposome, the retinoid is vitamin A, and the drug is an siRNA that targets HSP47.

* * * * *

UNITED STATES PATENT AND TRADEMARK OFFICE
CERTIFICATE OF CORRECTION

PATENT NO. : 8,178,124 B2
APPLICATION NO. : 13/249072
DATED : May 15, 2012
INVENTOR(S) : Yoshiro Niitsu et al.

It is certified that error appears in the above-identified patent and that said Letters Patent is hereby corrected as shown below:

On page 2, Column 1 (Item 56), Line 31, under Other Publications, please delete "Parenchmal" and insert --Parenchymal-- therefor.

On page 2, Column 1 (Item 56), Line 37, under Other Publications, please delete "Nonmenclature" and insert --Nomenclature-- therefor.

On page 2, Column 2 (Item 56), Line 12, under Other Publications, please delete "dimentylnitrosame" and insert --dimethylnitrosamine-- therefor.

On page 2, Column 2 (Item 56), Line 14, under Other Publications, please delete "6-phosphateyinsulin" and insert --6-phosphate insulin-- therefor.

On page 3, Column 1 (Item 56), Line 36, under Other Publications, please delete "M5076-Heptatic" and insert --M5076-Hepatic-- therefor.

On page 3, Column 2 (Item 56), Line 10, under Other Publications, please delete "Drosphila" and insert --Drosophila-- therefor.

On page 3, Column 2 (Item 56), Line 13, under Other Publications, please delete "Polylysine-Retinalddehyde" and insert --Polylysine-Retinaldehyde-- therefor.

On page 3, Column 2 (Item 56), Line 14, under Other Publications, please delete "Bilogical" and insert --Biological-- therefor.

On page 3, Column 2 (Item 56), Line 17, under Other Publications, please delete "Gastroentero!'" and insert --Gastroenterol.-- therefor.

On page 3, Column 2 (Item 56), Line 21, under Other Publications, please delete "Jounal," and insert --Journal,-- therefor.

In Column 3, Line 21, please delete "by" and insert --bp-- therefor.

In Column 5, Line 46, after "thereof" insert --.--.

In Column 5, Line 55, after "thereof" insert --.--.

Signed and Sealed this
Eighteenth Day of December, 2012

David J. Kappos
*Director of the United States Patent and Trademark Office*

CERTIFICATE OF CORRECTION (continued)
U.S. Pat. No. 8,178,124 B2

In Column 13, Line 37, please delete "siRNA$_{13}$finder" and insert --siRNA_finder-- therefor.

In Column 14, Line 52, please delete "200" and insert --200 µL,-- therefor.

In Column 15, Line 12, please delete "aSMA" and insert --αSMA-- therefor.

In Column 15, Line 15, please delete "anti-aSMA" and insert --anti-αSMA-- therefor.

SEQUENCE LISTING

<160> NUMBER OF SEQ ID NOS: 3

<210> SEQ ID NO 1

-continued

```
<211> LENGTH: 25
<212> TYPE: RNA
<213> ORGANISM: Artificial Sequence
<220> FEATURE:
<223> OTHER INFORMATION: siRNA for rat gp46

<400> SEQUENCE: 1
guuccaccau aagaugguag acaac                                      25

<210> SEQ ID NO 2
<211> LENGTH: 25
<212> TYPE: RNA
<213> ORGANISM: Artificial Sequence
<220> FEATURE:
<223> OTHER INFORMATION: siRNA for rat gp46

<400> SEQUENCE: 2
ccacaaguuu uauauccaau cuagc                                      25

<210> SEQ ID NO 3
<211> LENGTH: 19
<212> TYPE: RNA
<213> ORGANISM: Artificial Sequence
<220> FEATURE:
<223> OTHER INFORMATION: siRNA for rat gp46

<400> SEQUENCE: 3
gaaaccugua gaggccgca                                             19
```